US011160843B2

(12) United States Patent
Chang et al.

(10) Patent No.: US 11,160,843 B2
(45) Date of Patent: Nov. 2, 2021

(54) OXYTOCIN AND OPIOID ANTAGONISTS FOR TREATMENT OF SOCIAL DYSFUNCTION DISORDER

(71) Applicant: YALE UNIVERSITY, New Haven, CT (US)

(72) Inventors: Wohn Chui Chang, Woodbridge, CT (US); Olga Dal Monte, New Haven, CT (US); Matthew Piva, New Haven, CT (US)

(73) Assignee: Yale University, New Haven, CT (US)

( * ) Notice: Subject to any disclaimer, the term of this patent is extended or adjusted under 35 U.S.C. 154(b) by 23 days.

(21) Appl. No.: 16/398,744

(22) Filed: Apr. 30, 2019

(65) Prior Publication Data

US 2019/0328830 A1 Oct. 31, 2019

Related U.S. Application Data

(60) Provisional application No. 62/664,736, filed on Apr. 30, 2018.

(51) Int. Cl.
*A61K 38/095* (2019.01)
*A61K 9/00* (2006.01)
*A61P 25/00* (2006.01)

(52) U.S. Cl.
CPC .......... *A61K 38/095* (2019.01); *A61K 9/0073* (2013.01); *A61P 25/00* (2018.01); *A61K 9/0078* (2013.01)

(58) Field of Classification Search
None
See application file for complete search history.

(56) References Cited

U.S. PATENT DOCUMENTS

| 2007/0032410 A1 | 2/2007 | Quay et al. | |
| 2011/0065628 A1* | 3/2011 | Johnson | A61K 31/4178 514/1.1 |
| 2012/0128683 A1 | 5/2012 | Shantha | |
| 2013/0085106 A1* | 4/2013 | Pedersen | A61P 25/34 514/11.6 |

FOREIGN PATENT DOCUMENTS

WO WO 2009/035473 * 3/2009 .......... A61P 31/4015

OTHER PUBLICATIONS

Article downloaded from US Pharmacist website: https://www.uspharmacist.com/article/once-opioid-treatment-begins-naltrexone-as-effective-as-buprenorphinenaloxone, no authors listed; originally published Nov. 29, 2017; 3 pages total (Year: 2017).*
Anagnostou, et al., "Intranasal oxytocin versus placebo in the treatment of adults with autism spectrum disorders: a randomized controlled trial", Mol Autism. 3(1), Dec. 2012, 16.
Andari, et al., "Promoting social behavior with oxytocin in high-functioning autism spectrum disorders", Proc. Natl. Acad. Sci. USA. 107, Mar. 2010, 4389-4394.
Bicknell, et al., "Endogenous opiates regulate oxytocin but not vasopressin secretion from the neurohypophysis", Nature 298(5870), Jul. 1982, 161-162.
Campbell, et al., "Naltrexone in autistic children: a double-blind and placebo-controlled study", Psychopharmacol Bull. 26(1), 1990, 130-135 (Abstract only).
Chang, et al., "Inhaled oxytocin amplifies both vicarious reinforcement and self reinforcement in rhesus macaques (Macaca mulatta)", Proc. Natl. Acad. Sci. USA 109, Jan. 2012, 959-964.
Chang, "Supralinearly modulating social gaze dynamics with oxytocin under opioid antagonism", The Society for Social Neuroscience, 2016 Annual Meeting, San Diego, Book of Abstracts, Nov. 2016, 11-12 (abstract only).
Dadds, et al., "Nasal oxytocin for social deficits in childhood autism: a randomized clinical trial", J Autism Dev Disord. 44(3), Mar. 2014, 521-531.
Dal Monte, et al., "CSF and blood oxytocin concentration changes following intranasal delivery in macaque", PLoS One. 9(8), Aug. 2014, e103677.
Dal Monte, "Live interaction distinctively shapes social gaze dynamics in rhesus macaques", J Neurophysiol. 116(4), Oct. 2016, 1626-1643.
Dal Monte, et al., "Oxytocin enhances attention to the eye region in rhesus monkeys", Front. Neurosci. 8(41), Mar. 2014, 1-8.
Dal Monte, et al., "Oxytocin under opioid antagonism leads to supralinear enhancement of social attention", Proc. Natl. Acad. Sci.114, May 2017, 5247-5252.
Domes, et al., "Oxytocin improves "mind-reading" in humans", Biol. Psychiatry. 61, Mar. 2007, 731-733.
Gordon, et al., "Oxytocin enhances brain function in children with autism", Proc Natl Acad Sci U S A. 110(52), Dec. 2013, 20953-20958.
Guastella, et al., "Intranasal oxytocin improves emotion recognition for youth with autism spectrum disorders", Biol. Psychiatry. 67, Apr. 2010, 692-694.
Guastella, et al., "Oxytocin increase gaze to the eye region of human faces", Biol. Psychiatry. 63, Jan. 2008, 3-5.
Hathaway, et al., "Combination approach may help combat autism", Yale News, May 1, 2017, https://news.yale.edu/2017/05/01/combination-approach-may-help-combat-autism (accessed Aug. 2, 2020).
Hollander, et al., "Oxytocin infusion reduces repetitive behaviors in adults with autistic and Asperger's disorders", Neuropsychopharm. 28, Jan. 2003, 193-198.

(Continued)

*Primary Examiner* — Christina M Borgeest
(74) *Attorney, Agent, or Firm* — Saul Ewing Arnstein & Lehr LLP; Kathryn Doyle; Domingos J. Silva

(57) ABSTRACT

The present invention relates to the discovery that co-administration of both oxytocin (OT) and at least one opioid antagonist can increase social function in a subject. In certain embodiments, the co-administration can be used to treat one or more social dysfunction disorders in a subject, including, but not limited to autism, schizophrenia, anxiety disorders and post-traumatic stress disorder (PTSD). In other embodiments, the OT and the opioid antagonist can be co-administered to a subject as an aerosolized pharmaceutical composition.

18 Claims, 22 Drawing Sheets

Specification includes a Sequence Listing.

(56) References Cited

OTHER PUBLICATIONS

Leboyer, et al., "Brief report: a double-blind study of naltrexone in infantile autism", J Autism Dev Disord. 22(2), Jun. 1992, 309-319.
Leng, et al., "Naloxone potentiates the release of oxytocin induced by systemic administration of cholecystokinin without enhancing the electrical activity of supraoptic oxytocin neurones", Experimental Brain Research 88, 1992, 321-325.
Naples, et al., "Event-related potentials index neural response to eye contact", Biol Psychol. 127, Jul. 2017, 18-24.
Piva, et al., "Supralinear effects of combined oxytocin administration and opioid blockade on contingent social gaze dynamics", The Society for Social Neuroscience, 2016 Annual Meeting, San Diego, Book of Abstracts, A39, Nov. 2016, 30-31 (abstract only).
Spengler, et al., "Kinetics and Dose Dependency of Intranasal Oxytocin Effects on Amygdala Reactivity", Biol Psychiatry. 82(12), Dec. 2017, 885-894.
Williams, et al., "Brief report: case reports on naltrexone use in children with autism: controlled observations regarding benefits and practical issues of medication management", J Autism Dev Disord. 31(1), Feb. 2001, 103-108.
Yatawara, et al., "The effect of oxytocin nasal spray on social interaction deficits observed in young children with autism: a randomized clinical crossover trial", Mol Psychiatry. 21(9), Sep. 2016, 1225-1231.

\* cited by examiner

Live gaze interaction task

Mutual reward task

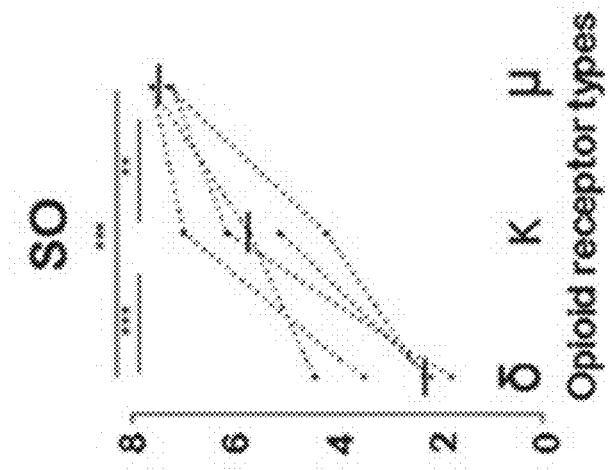
FIG. 10B LHT
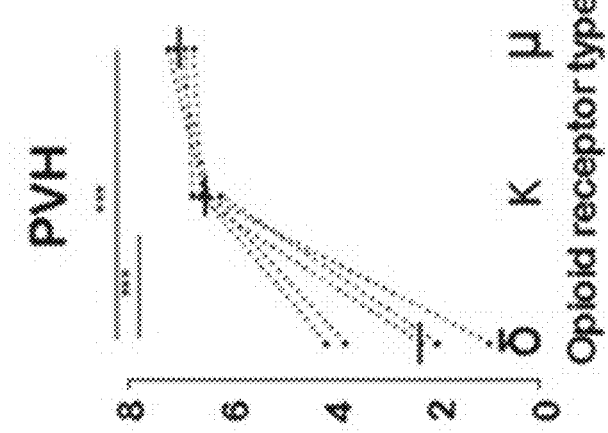
FIG. 10C PVH
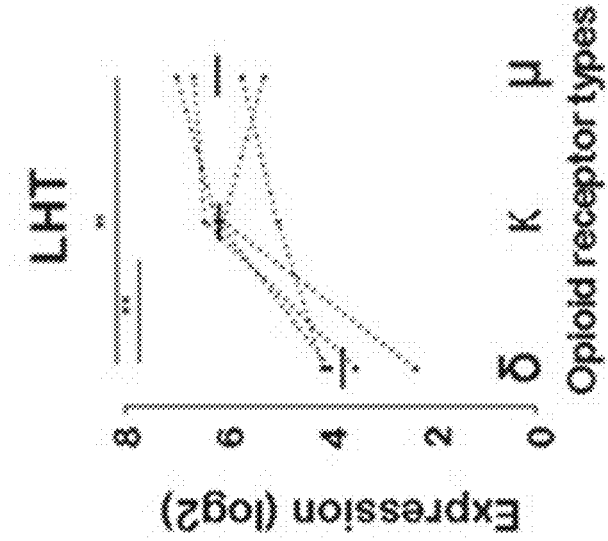
FIG. 10D SO

OXYTOCIN AND OPIOID ANTAGONISTS FOR TREATMENT OF SOCIAL DYSFUNCTION DISORDER

CROSS-REFERENCE TO RELATED APPLICATION

This application claims priority under 35 U.S.C. § 119(e) to U.S. Provisional Patent Application Ser. No. 62/664,736, filed Apr. 30, 2018, the disclosure of which is incorporated herein by reference in its entirety.

BACKGROUND OF THE INVENTION

There has been an increase in studies using oxytocin (OT) for improving social cognition in patients suffering from a range of conditions including autism, schizophrenia, anxiety disorders and post-traumatic stress disorder (PTSD). The results of many of these studies, however, have been inconsistent or inconclusive due to weak efficacy or irreproducibility.

The opioid system has been implicated in regulating social behavior. Excessive opioid activity in the brain has been suggested as a possible link to the development of early childhood autism. Abnormalities in central opioid levels have been observed in some individuals with autism; in fact, clinical trials with predominantly μ-opioid blockers, such as naltrexone or naloxone (NAL), have yielded promising results in ameliorating both social and nonsocial deficits. Specifically, μ-opioid receptors have been studied in relation to reward, emotion, and behavior in the social domain, and are strongly expressed in reward-related regions of the primate brain. In rhesus macaques, carrying the G allele of the μ-opioid receptor gene OPRM1, compared with homozygous C alleles, is associated with stronger maternal attachment in infants and more effective prevention of infant separation in mothers. Additionally, opioid agonists, such as morphine, decrease physical contact between social partners, whereas NAL administration increases solicitation for social contact, such as grooming and proximity.

There remains a need in the art for novel therapies for the treatment of disorders related to cognitive social dysfunction. In certain embodiments, such therapies can help treat at least one disorder selected from autism, Asperger's syndrome, pervasive developmental disorder not otherwise specified (PDD-NOS), Rett's disorder, childhood disintegrative disorder, semantic communication disorder, non-verbal learning disabilities, hyperlexia, schizophrenia, addiction, attention deficit disorder (ADD), depression, bi-polar depression, anxiety disorders, psychopathy, and post-traumatic stress disorder (PTSD). The present invention meets these needs.

BRIEF SUMMARY OF THE INVENTION

The present disclosure provides a method of increasing or preventing decrease of social cognition in a subject. In certain embodiments, the method comprises administering to the subject a therapeutically effective amount of oxytocin. In other embodiments, the subject is further administered a therapeutically effective amount of at least one opioid antagonist.

The present disclosure further provides a pharmaceutical compositions comprising oxytocin, at least one opioid antagonist, and at least one pharmaceutically acceptable carrier.

BRIEF DESCRIPTION OF THE DRAWINGS

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

FIG. 1A is an illustration of the live gaze interaction task used for examining social attention and its dynamics following mutual eye contact. The gaze positions of both monkeys in a given pair were recorded simultaneously and continuously. FIG. 1B is an illustration of the mutual reward task used to examine the impact of context in social attention dynamics. This task setup was identical to the live gaze interaction task but included a tone that predicted mutual juice rewards or no juice rewards to both monkeys at equal probabilities after 1.5 s. The intertone interval between the tones was jittered from 4 to 16 s. FIG. 1C is an illustration of the free-viewing task used to obtain an intranasal NAL dose-response curve. After fixating their gaze at the central target, monkeys viewed images for 15 s, followed by a reward in the form of a drop of juice.

FIG. 2A is a graph of overall frequency of fixations to the faces of conspecifics (upper line) and to humans (lower line, heterospecifics with similar facial features) after intranasally administering 0.5 mg, 1 mg, and 2 mg of NAL, normalized by the SAL condition. FIG. 2B is a graph showing frequency of fixations specifically to the eyes.

FIG. 3A is an averaged heat map showing gaze fixations in the OTNAL condition over the SAL condition. FIG. 3B is an averaged heat map showing fixations in the OTNAL condition over the summed effects of OT and NAL administered independently, demonstrating the supralinear effects. FIG. 3C is a graph showing the overall frequency of gaze fixations to the face of a conspecific in the OT (second from left bar), NAL (second from right bar), and OTNAL (right bar) conditions, normalized by the SAL (left bar) condition. FIG. 3D is a graph showing the effect size of OTNAL compared with the summed effect size of OT and NAL administered independently. FIGS. 3E-3F are graphs showing overall frequency of gaze fixations to the eyes of a conspecific in the same format as in FIGS. 3C and 3D. **P<0.01 over SAL condition, one-way ANOVA with Tukey-Kramer post hoc tests for multiple comparisons.

FIG. 4A is a graph of overall fixation duration to the face of a conspecific in the OT (second from left bar), NAL (second from right bar), and OTNAL (right bar) conditions, normalized by the SAL (left bar) condition. FIG. 4B is a graph of overall fixation duration to the eyes of a conspecific in the same format as in FIG. 4A.

FIG. 5A is a graph of peristimulus time histograms (PSTHs), aligned to mutual eye contact, showing the proportion of looking at the eyes following mutual eye contact in SAL (green), OT (blue), NAL (red), and OTNAL (purple) conditions. Horizontal marks indicate 10-ms time bins with significant differences (P<0.05, OT over SAL, blue; P<0.05, OTNAL over SAL, purple; P<0.01, yellow; paired-sample t tests). FIG. 5B is a graph showing the effects size of OTNAL compared with the added effect size of OT and NAL alone for 0.5-3 s after mutual eye contact. FIG. 5C is a graph of PSTH aligned to nonmutual eye contact in the same format as in A.

FIG. 7A is a PSTH showing the proportion of looking at the face following a tone predicting mutual reward in SAL (green), OT (blue), NAL (red), and OTNAL (purple) conditions. Reward occurred simultaneously for both monkeys 1.5 s after an unpredictable auditory tone. Horizontal marks indicate 10-ms time bins with significant differences (P<0.05, OTNAL over SAL, purple; P<0.01, yellow; paired-sample t tests). FIG. 7B is a graph showing the effects size of OTNAL versus the summed effect size of OT and NAL alone for 1.5-3.5 s after tone. FIG. 7C is a PSTH aligned to tones that did not result in reward to either monkey in the same format as in FIG. 7A. No 10-ms time bin for any drug condition was significantly higher than SAL (all P>0.05, paired-sample t tests).

FIG. 8A is a PSTH showing the proportion of looking at the mouth following the tone predicting mutual reward receipt in the SAL (green), OT (blue), NAL (red), and OTNAL (purple) conditions. Reward occurred simultaneously for both monkeys 1.5 s after the tone. Horizontal marks indicate 10-ms time bins with significant differences (P<0.05, OT over SAL, blue; P<0.05, OTNAL over SAL, purple; P<0.01, yellow; paired-sample t tests). FIG. 8B is a PSTH showing the proportion of looking at the mouth aligned to tones that did not result in reward to either monkey (same format as in FIG. 8A). No 10-ms time bin for any drug condition was significantly higher than for SAL (all P>0.05, paired sample t tests). FIG. 8C is a graph showing the effect size of OTNAL versus the summed effect size of OT and NAL alone for 1.5-3.5 s after mutual eye contact. FIGS. 8D-8E are graphs having the same format as in FIGS. 8A-8B: a PSTH showing the proportion of looking at the eyes following a tone predicting mutual reward (FIG. 8D), and a PSTH showing the proportion of looking at the eyes aligned to tones that did not result in reward to either monkey (FIG. 8E). No 10-ms time bin for any drug condition was significantly higher than for SAL (all P>0.05, paired-sample t tests).

FIG. 9A is a graph of overall frequency of gaze fixations to the face of a conspecific in the OT, NAL, and OTNAL conditions, normalized by the SAL condition for males (left bars) and females (right bars). FIG. 9B is a graph of overall frequency of gaze fixations to the eyes of a conspecific in the same format as in FIG. 9A. FIG. 9C is a graph of the proportion of looking at the eyes following mutual eye contact in the OT, NAL, and OTNAL conditions, normalized by the SAL condition for males (left bars) and females (right bars). FIG. 9D is a graph of the proportion of looking at the face following mutual reward in the same format as in FIG. 9C.

FIG. 10A is a graph showing microarray expression of OXT and OXTR from 190 regions averaged across six postmortem human brains from the Allen Human Brain Atlas (AHBA). Ten tissue samples displayed OXT expression 1 SD above the mean: LHT, PVH, SO, dorsomedial hypothalamic nucleus (DMH), lateral hypothalamic area, anterior region (LHA), lateral hypothalamic area, medial region (LHM), ventral hypothalamic area, medial region (VHM), perifornical nucleus (PeF), posterior hypothalamic area (PHA), and preoptic region (PrOR). FIGS. 10B-10K are a set of graphs showing that μ-opioid and κ-opioid receptor genes are expressed significantly more than δ-opioid receptor genes across the top three OXT-enriched regions (FIGS. 10B-10D) and seven additional regions (FIGS. 10E-10K). Each line connects samples from the same donor. Different numbers of lines are due to non-uniform sampling across the six AHBA donors. The horizontal ticks indicate the mean of different donors. FIG. 10O shows that OXTR expression was consistently above average within OXT-enriched regions.

DETAILED DESCRIPTION OF THE INVENTION

Figure 1A:
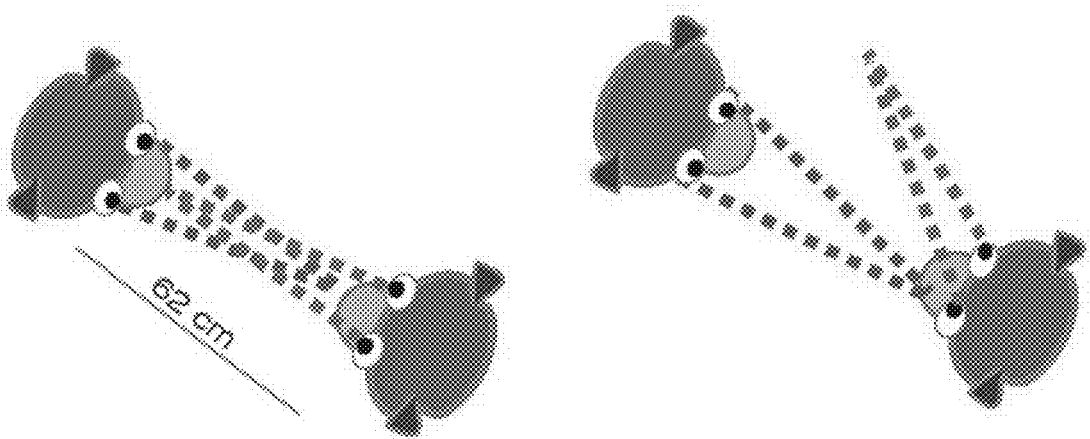
FIGS. 1A-1C are diagrams showing experimental designs used to test the oxytocin, naloxone and combination therapies of the invention.

The present invention relates in part to the discovery that co-administration of oxytocin (OT) and at least one opioid antagonist can increase social function in a subject. In certain embodiments, the co-administration can be used to treat one or more social dysfunction disorders in a subject, including, but not limited to autism, schizophrenia, anxiety disorders and post-traumatic stress disorder (PTSD). In other embodiments, the OT and the opioid antagonist can be co-administered to a subject via an aerosolized pharmaceutical composition.

Methods

In one aspect, the invention provides a method of increasing social cognition in a subject, the method comprising administering to the subject a therapeutically effective amount of both oxytocin and at least one opioid antagonist.

In certain embodiments, the method treats at least one social function disorder in the subject. In other embodiments, the at least one social function disorder is linked to abnormal oxytocin processing in the subject. In yet other embodiments, the at least one social function disorder is at least one selected from autism, autism spectrum disorders (ASD), Asperger's syndrome, pervasive developmental disorder not otherwise specified (PDD-NOS), Rett's disorder, childhood disintegrative disorder (CDD), semantic communication disorder, non-verbal learning disabilities, hyperlexia, schizophrenia, addiction, attention deficit disorder (ADD), depression, bi-polar depression, anxiety disorders, psychopathy, and post-traumatic stress disorder (PTSD).

In certain embodiments, the method treats or ameliorates at least one symptom of social dysfunction selected from inappropriate social interaction, difficulty with social interactions, difficulty with communication, generally diminished social attention, poor eye contact, persistent repetition of words or actions, compulsive behavior, impulsivity, self-harm, learning disability or speech delay, unawareness of others' emotions, anxiety, depression, and sensitivity to sound.

In certain embodiments, the at least one opioid antagonist is a compound selected from naltrexone, naloxone (NAL), nalmefene, diprenorphine, nalorphine, nalorphine dinicotinate, levallorphan, samidorphan, nalodiene, buprenorphine, dezocine, eptazocine, butorphanol, levorphanol, nalbuphine, pentazocine, phenazocine, cyprodime, naltrindole, norbinaltorphimine, and prodrugs, salts, and solvates thereof. In other embodiments, the at least one opioid antagonist is naloxone.

In certain embodiments, the therapeutically effective amount of oxytocin is about 0.4 µg/kg to about 0.8 µg/kg (oxytocin/subject weight). In other embodiments, the therapeutically effective amount of oxytocin is about 0.5 µg/kg to about 0.6 µg/kg (oxytocin/subject weight). In yet other embodiments, the therapeutically effective amount of oxytocin is about 0.1 µg/kg to about 10 µg/kg (oxytocin/subject weight). In yet other embodiments, the therapeutically effective amount of oxytocin is about 0.1 µg/kg (oxytocin/subject weight), about 0.2 µg/kg (oxytocin/subject weight), about 0.5 µg/kg (oxytocin/subject weight), about 1 µg/kg (oxytocin/subject weight), about 2 µg/kg (oxytocin/subject weight), about 3 µg/kg (oxytocin/subject weight), about 4 µg/kg (oxytocin/subject weight), about 5 µg/kg (oxytocin/subject weight), about 7 µg/kg (oxytocin/subject weight), about 8 µg/kg (oxytocin/subject weight), about 9 µg/kg (oxytocin/subject weight), about 10 µg/kg (oxytocin/subject weight), about 12 µg/kg (oxytocin/subject weight), about 15 µg/kg (oxytocin/subject weight), about 20 µg/kg (oxytocin/subject weight), about 30 µg/kg (oxytocin/subject weight), about 40 µg/kg (oxytocin/subject weight), about 50 µg/kg (oxytocin/subject weight), or any values therebetween.

In certain embodiments, the therapeutically effective amount of oxytocin is about 12 µg to about 96 µg. In other embodiments, the therapeutically effective amount of oxytocin is about 24 µg to about 72 µg. In yet other embodiments, the therapeutically effective amount of oxytocin is about 48 µg. In yet other embodiments, the therapeutically effective amount of oxytocin is about 1 µg, about 2 µg, about 5 µg, about 10 µg, about 20 µg, about 30 µg, about 40 µg, about 50 µg, about 75 µg, about 100 µg, about 150 µg, about 200 µg, or any values therebetween.

In certain embodiments, the therapeutically effective amount of the at least one opioid antagonist is about 0.008 mg/kg to about 0.005 mg/kg. In other embodiments, the therapeutically effective amount of the at least one opioid antagonist is about 0.016 mg/kg to about 0.033 mg/kg. In yet other embodiments, the therapeutically effective amount of the at least one opioid antagonist is about 0.001 mg/kg to about 1 mg/kg. In yet other embodiments, the therapeutically effective amount of the at least one opioid antagonist is about 0.001 mg/kg, about 0.005 mg/kg, about 0.01 mg/kg, about 0.02 mg/kg, about 0.05 mg/kg, about 0.075 mg/kg, about 0.1 mg/kg, about 0.2 mg/kg, about 0.5 mg/kg, about 1 mg/kg, about 2 mg/kg, about 5 mg/kg, about 10 mg/kg, or any values therebetween.

In certain embodiments, the therapeutically effective amount of the at least one opioid antagonist is about 0.25 mg to about 4 mg. In other embodiments, the therapeutically effective amount of the at least one opioid antagonist is about 0.5 mg to about 2 mg. In yet other embodiments, the therapeutically effective amount of the at least one opioid antagonist is about 1 mg. In yet other embodiments, the therapeutically effective amount of the at least one opioid antagonist is about 0.01 mg, about 0.05 mg, about 0.1 mg, about 0.2 mg, about 0.5 mg, about 0.75 mg, about 1 mg, about 2 mg, about 5 mg, about 10 mg, about 20 mg, about 50 mg, or any values therebetween.

In certain embodiments, the oxytocin and opioid antagonist are administered to the subject through a method selected from inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, epidural, intrapleural, intraperitoneal, subcutaneous, intramuscular, intradermal, intra-arterial, intravenous, intrabronchial, inhalation, and topical administration. In other embodiments, the administration is inhalational administration.

In certain embodiments, the oxytocin and opioid antagonist are co-formulated as part of a pharmaceutical composition further comprising at least one pharmaceutical carrier. In other embodiments, the at least one pharmaceutical carrier is sterile saline. In yet other embodiments, the pharmaceutical composition is formulated for pulmonary administration or inhalation administration.

In certain embodiments, the pharmaceutical composition is administered to the subject using an apparatus or device capable of aerosolizing the pharmaceutical composition. In other embodiments, the apparatus or device is at least one selected from a nebulizer, an inhalator, a humidifier, an inhaler, a nasal sprayer, a mister, and an atomizer.

In certain embodiments, the subject is a mammal. In other embodiments, the subject is a human.

Compositions

In another aspect, the invention provides a pharmaceutical compositions comprising oxytocin, at least one opioid antagonist and at least one pharmaceutically acceptable carrier.

In certain embodiments, the pharmaceutically acceptable carrier comprises at least one selected from the group consisting of sterile water, sterile saline, and an alcohol.

In certain embodiments, the at least one opioid antagonist is a compound selected from naltrexone, naloxone (NAL), nalmefene, diprenorphine, nalorphine, nalorphine dinicotinate, levallorphan, samidorphan, nalodiene, buprenorphine, dezocine, eptazocine, butorphanol, levorphanol, nalbuphine, pentazocine, phenazocine, cyprodime, naltrindole, norbinaltorphimine and prodrugs, salts and, solvates thereof. In other embodiments, the at least one opioid antagonist is naloxone.

In certain embodiments, the pharmaceutical composition comprises about 12 µg to about 96 µg oxytocin. In other embodiments, the pharmaceutical composition comprises about 24 µg to about 72 µg oxytocin. In yet other embodiments, the pharmaceutical composition comprises about 48 µg oxytocin.

In certain embodiments, the pharmaceutical composition comprises about 0.25 mg to about 4 mg of the at least one opioid antagonist. In other embodiments, the pharmaceutical composition comprises about 0.5 mg to about 2 mg of the at least one opioid antagonist. In yet other embodiments, the pharmaceutical composition comprises about 1 mg of the at least one opioid antagonist.

In certain embodiments, the pharmaceutical composition further comprises at least one additional ingredient selected from the group consisting of sodium acetate trihydrate, glacial acetic acid, chlorobutanol, benzalkonium chloride, disodium ethylenediametetraacetate, and hydrochloric acid.

Combination and Concurrent Therapies

In one embodiment, the compositions of the invention are useful in the methods of present invention when used concurrently with at least one additional compound useful for preventing and/or treating diseases and/or disorders contemplated herein.

In one embodiment, the compositions of the invention are useful in the methods of present invention in combination with at least one additional compound useful for preventing and/or treating diseases and/or disorders contemplated herein.

These additional compounds may comprise compounds of the present invention or other compounds, such as commercially available compounds, known to treat, prevent, or reduce the symptoms of diseases and/or disorders contemplated herein. In certain embodiments, the combination of at least one compound of the invention or a salt thereof, and at least one additional compound useful for preventing and/or treating diseases and/or disorders contemplated herein, has additive, complementary or synergistic effects in the prevention and/or treatment of diseases and/or disorders contemplated herein.

As used herein, combination of two or more compounds may refer to a composition wherein the individual compounds are physically mixed or wherein the individual compounds are physically separated. A combination therapy encompasses administering the components separately to produce the desired additive, complementary or synergistic effects.

A synergistic effect may be calculated, for example, using suitable methods such as, for example, the Sigmoid-$E_{max}$, equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326), the median-effect equation (Chou & Talalay, 1984, Adv. Enzyme Regul. 22: 27-55), and through the use of isobolograms (Tallarida & Raffa, 1996, Life Sci. 58: 23-28). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosing

The regimen of administration may affect what constitutes an effective amount. The therapeutic formulations may be administered to the patient either prior to or after the onset of a disease and/or disorder contemplated herein. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease and/or disorder contemplated herein. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 µg/kg to 100 mg/kg of body weight/per day. One of ordinary skill in the art would be able to study the relevant factors and make the determination regarding the effective amount of the therapeutic compound without undue experimentation.

The compound may be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease and/or disorder contemplated herein.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physician taking all other factors about the patient into account.

In some embodiments, the dose of a compound of the invention is from about 0.5 µg to about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of the disease and/or disorder contemplated herein.

The term "container" includes any receptacle for holding the pharmaceutical composition or for managing stability or water uptake. For example, in certain embodiments, the container is the packaging that contains the pharmaceutical composition, such as liquid (solution and suspension), semi-solid, lyophilized solid, solution and powder or lyophilized formulation present in dual chambers. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease and/or disorder contemplated herein.

Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, epidural, intrapleural, intraperitoneal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, emulsions, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Pulmonary Administration

A pharmaceutical composition of the invention may be prepared, packaged, or sold in a formulation suitable for pulmonary administration via the buccal cavity. Such a formulation may comprise dry particles that comprise the active ingredient and have a diameter in the range from about 0.5 to about 7 nanometers, and in certain embodiments from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. In certain embodiments, such powders comprise particles wherein at least 98% of the particles by weight have a diameter greater than 0.5 nanometers and at least 95% of the particles by number have a diameter less than 7 nanometers. In certain embodiments, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (in certain embodiments having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration in certain embodiments have an average diameter in the range from about 0.1 to about 200 nanometers.

The pharmaceutical composition of the invention may be delivered using an inhalator such as those recited in U.S. Pat. No. 8,333,192 B2, which is incorporated herein by reference in its entirety.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares. Formulations suitable for nasal administration may, for example, comprise from about as little as 0.1% (w/w) and as much as 100% (w/w) of the active ingredient, and may further comprise one or more of the additional ingredients described herein.

In certain embodiments, the opioid antagonist is formulated for inhalation administration according to the formulations disclosed in PCT Application Publication WO/2015/095644A1 and U.S. Patent Application Publication No. US2015/0174061.

In certain embodiments, the oxytocin is formulated for inhalation administration according to the formulations disclosed in European Patent Application Publication EP20080163932 and U.S. Patent Application Publication No. US2011/0237508.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone. One acceptable vehicle for topical delivery of some of the compositions of the invention may contain liposomes.

Buccal Administration

A pharmaceutical composition of the invention may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, separation science and organic chemistry are those well-known and commonly employed in the art. It should be understood that the order of steps or order for performing certain actions is immaterial, so long as the present teachings remain operable. Moreover, two or more steps or actions can be conducted simultaneously or not.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, nasal, pulmonary and topical administration.

A "disease" as used herein is a state of health of an animal wherein the animal cannot maintain homeostasis, and wherein if the disease is not ameliorated then the animal's health continues to deteriorate.

A "disorder" as used herein in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "international unit" or "IU" refers to a unit of measurement for a pharmaceutical substance that varies based on the identity of the substance being measured, based on the biological activity or effect of the substance. Commonly, international units are used to quantify vitamins, hormones, medications, vaccines and biologics. In certain embodiments, oxytocin can be measured in IU's, such that 1 IU of oxytocin is equivalent to 2 μg of pure oxytocin peptide.

As used herein, the term "oxytocin" refers to Cys Tyr Ile Gln Asn Cys Pro Leu Gly-NH$_2$ with a disulfide bridge between the 2 Cys residues (SEQ ID NO: 1), or 1-({(4R, 7S,10S,13S,16S,19R)-19-amino-7-(2-amino-2-oxoethyl)-10-(3-amino-3-oxopropyl)-16-(4-hydroxybenzyl)-13-[(1S)-1-methylpropyl]-6,9,12,15,18-pentaoxo-1,2-dithia-5,8,11,14,17-pentaazacycloicosan-4-yl}carbonyl)-L-prolyl-L-leucylglycinamide, or a salt or solvate thereof:

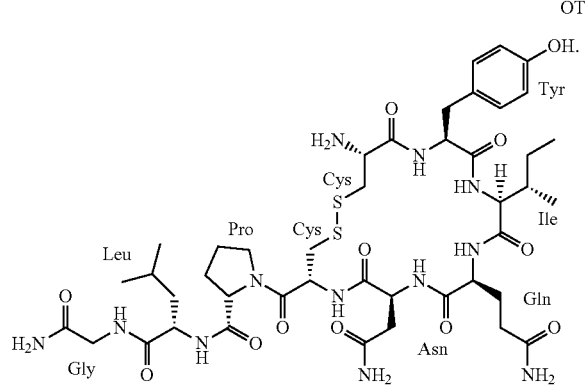

The terms "patient," "subject" or "individual" are used interchangeably herein, and refer to any animal, or cells thereof whether in vitro or in situ, amenable to the methods described herein. In a non-limiting embodiment, the patient, subject or individual is a human. In other embodiments, the patient is a non-human mammal including, for example, livestock and pets, such as ovine, bovine, porcine, canine, feline and murine mammals. In yet other embodiments, the patient is an avian animal or bird. Preferably, the patient, individual or subject is human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

The term "prevent," "preventing" or "prevention," as used herein, means avoiding or delaying the onset of symptoms associated with a disease or condition in a subject that has not developed such symptoms at the time the administering of an agent or compound commences.

A "therapeutic" treatment is a treatment administered to a subject who exhibits signs of pathology, for the purpose of diminishing or eliminating those signs.

As used herein, the term "therapeutically effective amount" refers to an amount that is sufficient or effective to prevent or treat (delay or prevent the onset of, prevent the progression of, inhibit, decrease or reverse) a disease or condition described or contemplated herein, including alleviating symptoms of such disease or condition.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein or a symptom of a condition contemplated herein, with the purpose to cure, heal, alleviate, relieve, alter, remedy, ameliorate, improve, or affect a condition contemplated herein or the symptoms of a condition contemplated herein. Such treatments may be specifically tailored or modified, based on knowledge obtained from the field of pharmacogenomics.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual and partial numbers within that range, for example, 1, 2, 2.7, 3, 4, 5, 5.3, and 6. This applies regardless of the breadth of the range.

The following abbreviations are used herein: ADD, attention deficit disorder; NAL, naloxone; OT, oxytocin; OTNAL, co-administered oxytocin and naloxone; PDD-NOS, pervasive developmental disorder not otherwise specified; PSTHs, Peristimulus time histograms; PTSD, post-traumatic stress disorder; ROI, region of interest; SAL, saline.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Animals and Surgical Procedure:

Nine adult rhesus macaques (*Macaca mulatta*) were selected for study. The animals (six males and three females) were all housed together in a colony in either pairs or triads. Each animal was kept on a 12-h light/dark cycle and had access to food 24 h each day with controlled access to water during testing. Before testing began, each monkey received a surgically implanted head post (Crist Instruments, Gray Matter Research) for restraining its head while tracking eye positions. At the time of surgery, anesthesia was induced with ketamine hydrochloride (10 mg/kg i.m.) and maintained with isoflurane (1.0-3.0%, to effect). Aseptic procedures were used, and heart rate, respiration rate, blood pressure, expired $CO_2$, and body temperature were monitored throughout the procedure. Monkeys were allowed an additional 30-40 d of recovery after the implant surgery.

Pharmacological Manipulations:

All of the tested subjects received pharmacological manipulations through a pediatric nebulizer (PARI Baby Nebulizer; PARI Respiratory Equipment) with a cone-shaped facemask. The facemask, designed for canine anesthesia, was fitted entirely over the muzzle area, and the subject breathed freely through the nose for the duration of the dose administration. Before experimental sessions, monkeys were first incrementally habituated to the facemask and then to the nebulizer until they were completely relaxed during the procedure, which typically took about 3-5 d. This habituation procedure was performed with saline (SAL). During both the habituation phase and the testing phase, the animals' heads were restrained to minimize movement and enhance administration reliability. Each of the different pharmacology manipulations tested was diluted to a volume of 2 mL using sterile SAL and was administered over the course of 8-10 min. In addition, experimental sessions were conducted at the same time of day to control for diurnal fluctuations. Behavioral testing began 30 min after each treatment. A "within-subjects" design was used so that each animal experienced all drug conditions with a randomized order on consecutive days of administration across animals.

Calibration Procedures.

Gaze calibration procedures for studying dyadic gaze interactions reported by Dal Monte, et al., 2016, J. Neurophysiol. 116:1626-1643 were used here. Briefly, before each experimental session, each of the two animals underwent a systematic calibration procedure. Subjects were required to fixate on a specific point at a specific time to estimate the viewing angle based on a temporarily placed screen (36 cm away from the subject's eyes, located exactly in middle distance between the two subjects). Stimuli were controlled by the Psychtoolbox and Eyelink toolbox in MATLAB (MathWorks) (Brainard, 1997, Spat Vis 10:433-436). The identical procedure was repeated for the second animal. For analysis purposes, the location was determined where the animal was looking on a theoretical screen located further from the actual screen on which the animal was calibrated. With trigonometric corrections, the ROIs were identified and matched based on individual measurements of each monkey's face to the dimension of fixations as measured from the calibration screen. Fixations were then mapped in detail across the face of the conspecific.

Live Gaze Interaction Task:

Two animals sat in front of each other with no task constraints while the eye positions of both animals were recorded simultaneously and continuously (FIG. 1A). Horizontal and vertical eye positions were sampled at 1,000 Hz using two infrared eye monitor camera systems (Eyelink; SR Research). The two monkeys were positioned 62 cm apart from one another, with the top of each monkey's head at 76 cm from the floor. Before starting to record gaze behavior, each animal underwent a systematic calibration procedure (see Calibration procedures). During the calibration and until the beginning of each session, the two animals had no visual access to each other, with a screen fully separating the view of both animals. The screen was lifted at the start of each session, marking the beginning of the live gaze interaction task. Each session lasted 3 min, for a total of eight sessions each day, with a 3-min break between sessions with no visual access. One of the two animals in a given pair was administered a drug via nebulizer (see Pharmacological manipulations) corresponding to one of the four pharmacology conditions: OT (24 IU), NAL (1 mg), SAL, or the combination of OT (24 IU) and NAL (1 mg) together (OTNAL). Behavioral testing began 30 min after each treatment and lasted for about 45 min. A total of five animals (three males and two females) with between three and five distinct conspecifics (total of 20 pairs) participated in all four pharmacology conditions. 640 sessions were collected in total: 32 sessions for each drug condition per subject.

Figure 1B:
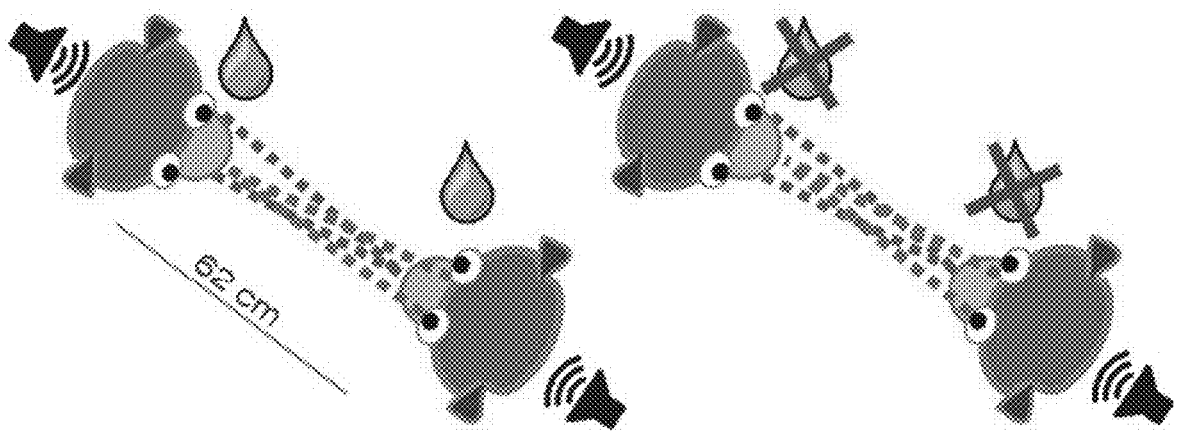
Figure 1B:
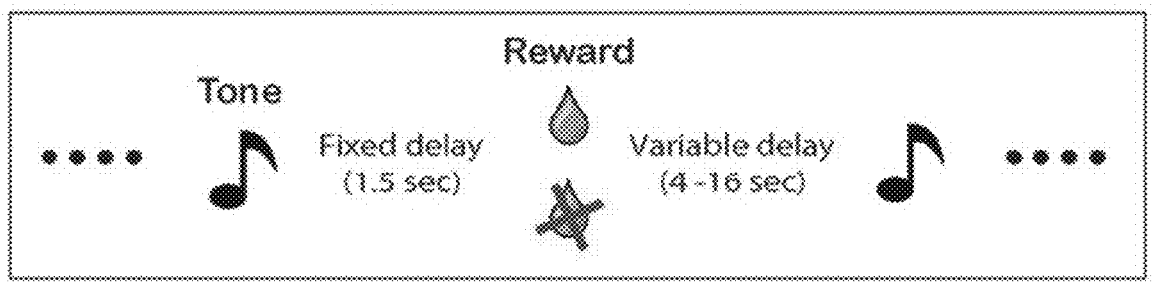

Mutual Reward Task:

Animals were placed in the same configuration as in the live gaze interaction task. In this task, two speakers (each speaker located by the chair of each monkey) and two juice tubes, one for each monkey, were added to the setup. An auditory tone was played at random time intervals (between 4 and 16 s). Following the tone, simultaneous juice rewards to both monkeys (0.5 mL) or no rewards to both monkeys could occur at equal probabilities after 1.5 s (FIG. 1B). Before and between these sessions, an occluder was placed between the animals. Similar to the live gaze interaction task, the eye movements of both animals were completely unconstrained, allowing for examination of naturalistic gaze patterns, and one of the two animals in a given pair was administered one of the four drugs via a nebulizer. Each session lasted 5 min, for a total of four sessions each day, with a 3-min break between sessions with no visual access. A total of five animals (three males and two females) with between three and five distinct conspecifics (total of 20 pairs) participated in all four drug conditions. 320 sessions were collected in total: 16 sessions for each drug condition per subject. The mutual reward task was always performed after the live gaze interaction task, ~75 min after administration of each drug, and lasted for about 30 min.

NAL Dose-Response Curve:

Although prior studies have suggested nasal spray as a reliable delivery route, no studies have investigated the effect of NAL on social behaviors in humans or nonhuman primates following intranasal administration. Therefore, to determine the optimal dosage of NAL for eliciting social effects, a preliminary dose-response study was completed for intranasal NAL (N7758; Sigma) administration in three animals (two male and one female adult rhesus monkeys) during the free-viewing task.

Figure 1C:
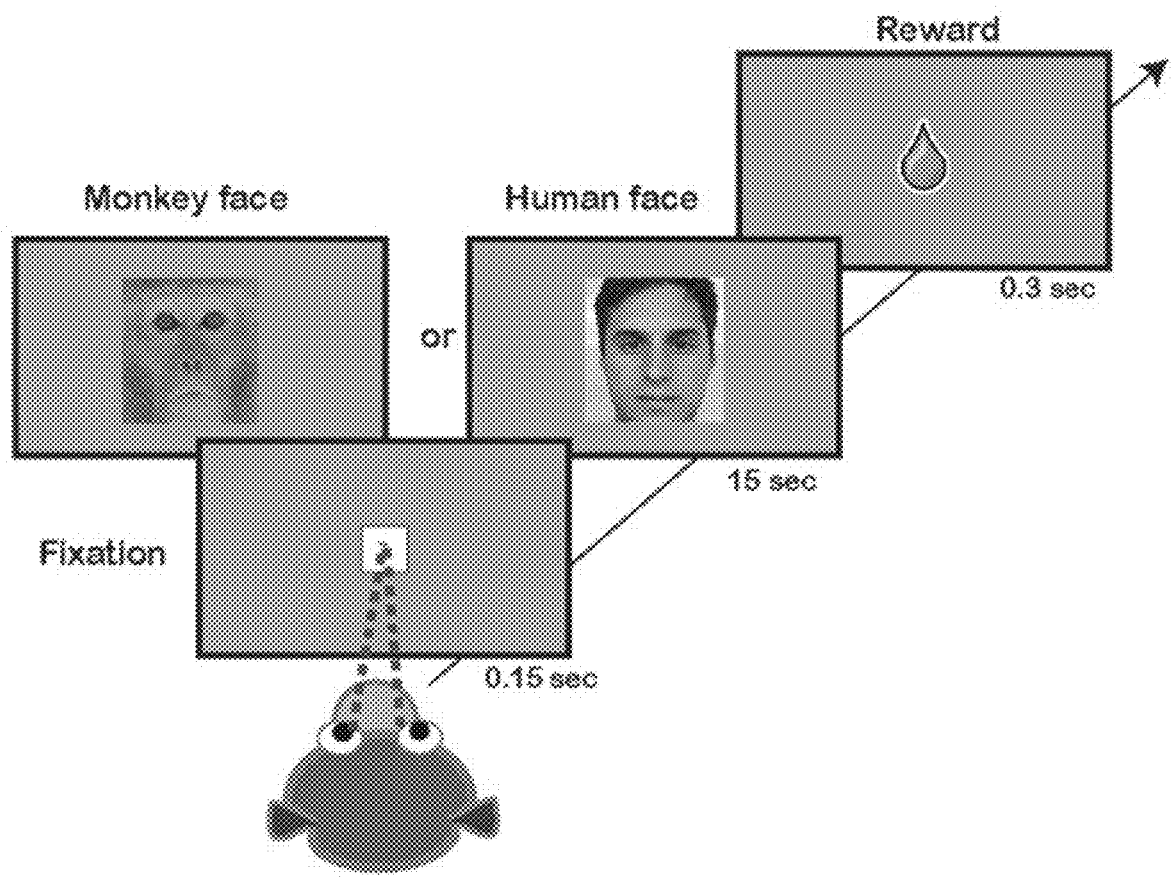

On the day of the experiment, monkeys were transported in a primate chair from the colony room to the experimental room. After restraining their heads, doses of 0.5 mg, 1 mg, or 2 mg of NAL or sterile SAL were administered with a nebulizer in a 2-mL volume of sterile SAL. Behavioral testing began 30 min after each treatment and lasted for about 150 min. Monkeys first acquired and held a central fixation point for 150 ms, followed by freely viewing images for 15 s. During the 15-s period, monkeys were free to explore, or not explore, each face presented while an infrared eye-tracking camera continuously recorded their eye positions (Eyelink; SR Research). At the end of the 15-s presentation, a juice reward (0.3 mL) was delivered, regardless of the gaze pattern of the subject (FIG. 1C). Images were presented randomly, and monkeys saw an average of 132±19 images per day. Each daily session used a different stimulus set. Each stimulus set contained 96 unique human and monkey faces (48 images each).

Similar experiments were conducted, incorporating OT. For OT (03251; Sigma), the conventional dose of 24 IU used in both humans and nonhuman primates was chosen. Fixation frequencies to the whole picture, as well as to the defined eye region, were obtained for each monkey for SAL, 0.5 mg of NAL, 1 mg of NAL, and 2 mg of NAL. Fixations to the face and eye regions were normalized for each of the three conditions by the SAL baseline for each animal. These normalized values were compared for fixations to the face and then for fixation to the eyes using ANOVA (with dose and image category as factors) and subsequent multiple comparison tests (Tukey-Kramer post hoc tests).

Fixation Analyses Over Entire Sessions:

Fixations to the defined eye regions were first obtained for each monkey, as were the fixations to the face and total fixations occurring in the setup for the SAL, NAL, OT, and OTNAL drug conditions. Fixations to the eye region and overall face were normalized in the NAL, OT, and OTNAL conditions by the SAL baseline within pairs, and pairs were then averaged within each drug condition (FIGS. 3A-3F). These values were compared with a one-way ANOVA (with condition as a factor) and subsequent multiple comparison tests (Tukey-Kramer post hoc tests). For measures of overall attention to the eyes and face of a conspecific, supralinearity was determined by comparing the effects of OTNAL with the summed effects of OT and NAL alone with a paired-sample t test. Correlation between these two measures was also evaluated via linear regression, with significance determined by an F test for the model.

Dynamic Gaze Analyses.

To measure gaze dynamics following mutual eye contact, mutual eye contact events were identified in which both animals initiated eye contact within a window measuring a 7.7°×3.8° visual angle. A 5-s window after each instance of mutual eye contact was examined to identify when and how long the monkey looked back into the eyes of the conspecific. Similarly, a 4-s window was taken after each tone that eventually predicted mutual reward. These 5-s and 4-s windows were chosen empirically based on the observation that looking behaviors return to a rough baseline, with no significant differences between drug groups observed after these periods (FIGS. 5A-5C, 7A-7C). 10-ms bins were used and binary datasets were created to characterize whether the animal was looking at the face of the conspecific within each bin. If a given animal looked back into the face of a conspecific at any time within a given 10-ms bin, that bin was given a value of 1. Otherwise, that bin was given a value of 0. Total amount of return viewing was summed over all instances of mutual eye contact on a given day of testing, normalized by the bin with the highest instance of returning gaze, and then averaged across pairs to compare quantitatively across drug conditions.

To analyze differences between drug groups, t tests were first performed to compare values at all bins within the 5-s periods after mutual eye contact. Windows of activity were defined in which gaze behavior between the two groups diverged (500-3,000 ms for mutual eye contact and 1,500-3,500 ms for mutual reward). Significant differences of drug conditions over the SAL baseline within these windows were determined with a permutation test by shuffling the data 1,000 times and randomly assigning the data from each monkey an identity in one of the groups (SAL baseline or a given drug group) being compared in each condition. The data were then averaged and compared, with a discrete value being obtained as the maximum difference between groups in some bin within the defined window. The permutated values were then sequentially ordered for determining threshold values for significance. To determine whether the findings were specific to periods following interactive events, non-mutual eye contact and tones after which reward was not administered to either monkey were aligned to.

To test whether discrete areas of the face were driving these differences in each condition, the ROIs were redefined for determining whether or not animals looked back at the conspecific. For mutual eye contact, two control analyses were conducted. The first control analysis retained mutual eye contact events, but instead measured attention to the mouth of the conspecific following eye contact. The second control analysis determined attention to the mouth of the conspecific following simultaneous gaze to the mouth ROI. The mouth region was defined with a window measuring 5.3°×8.0° visual angle. The same analyses were then repeated as mentioned above for these controls. For mutual reward receipt, the eye and mouth were examined individually to determine what smaller ROIs were driving overall attention to the face. After defining these two new ROIs, analyses identical to those analyses mentioned above were again applied. When comparing the effects of OT and NAL alone with the OTNAL combination condition, supralinearity was determined by first quantifying the effect sizes for OT, NAL, and OTNAL over the SAL baseline for mutual eye contact and mutual reward events.

This quantification analysis was accomplished by searching in the 500- to 3,000-ms window of activity for mutual eye contact and in the 1,500- to 3,500-ms window of activity for mutual reward for the time bin in which OTNAL had a maximal effect over SAL. This effect of OTNAL was then compared with the added maximal effects of the separate OT and NAL conditions over SAL with a paired-sample t test to determine significance. Correlation between these two measures was also evaluated via linear regression, with significance determined by the F-test for the model.

Data Visualization Using Heat Maps:

Fixation coordinates to the faces of conspecific monkeys were determined using the correction procedure described previously (Dal Monte, et al., 2016, J. Neurophysiol. 116: 1626-1643.). Heat maps were then plotted for each session based on fixations specifically to the face of the conspecific using the EyeMMV toolbox in MATLAB. Heat maps were based on the average number of fixations, measuring values within the SAL, NAL, OT, and OTNAL conditions to values ranging from less than 25 to greater than 250 fixations. Image dimensions were defined as 340×340 arbitrary units to align to the fixation data and binned at 20-unit intervals. Smoothing was accomplished using a Gaussian filter function in MATLAB. Fixations to the face of the conspecific were then averaged for all monkeys in a given condition and overlaid on a representative image of the face of one particular monkey. Difference heat maps were produced by comparing OTNAL over the SAL baseline (binned from less than −30 to greater than 60 fixation difference) as well as OTNAL over the added effects of the separate OT and NAL conditions (binned from less than −15 to greater than 30 fixation difference).

Figure 10A:
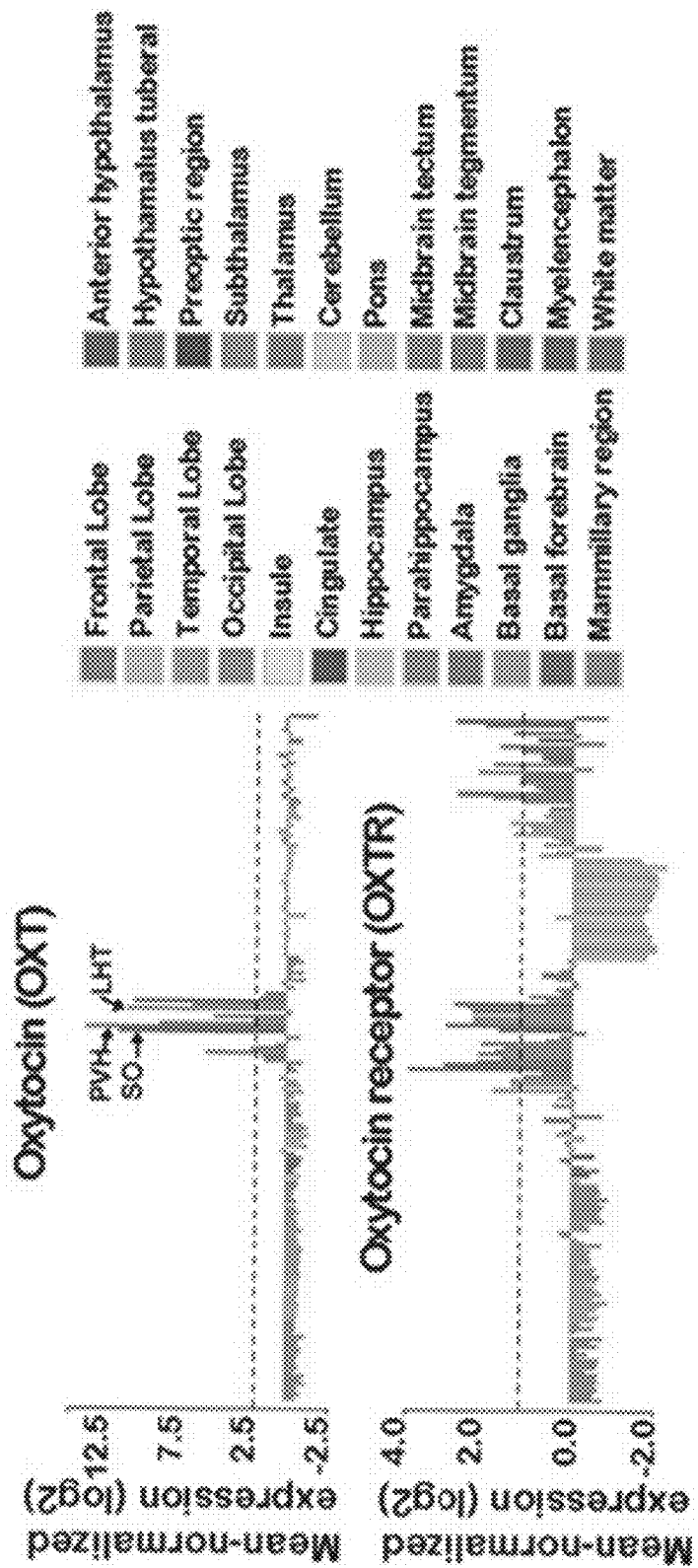
FIGS. 10A-10O are graphs showing certain gene expression patterns. As demonstrated herein, genes encoding μ-opioid and κ-opioid, but not δ-opioid, receptors display above-average expression in OT-enriched regions.
Figure 10E:
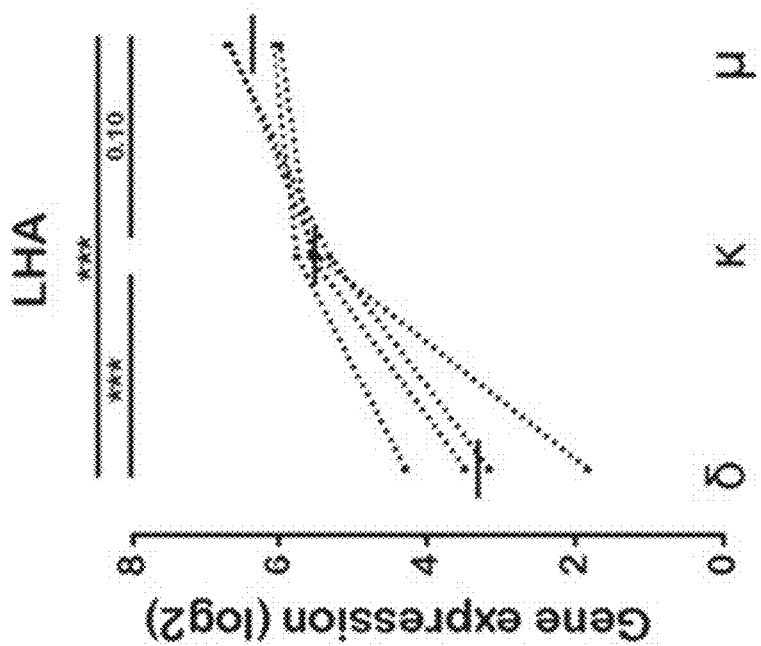
Figure 10F:
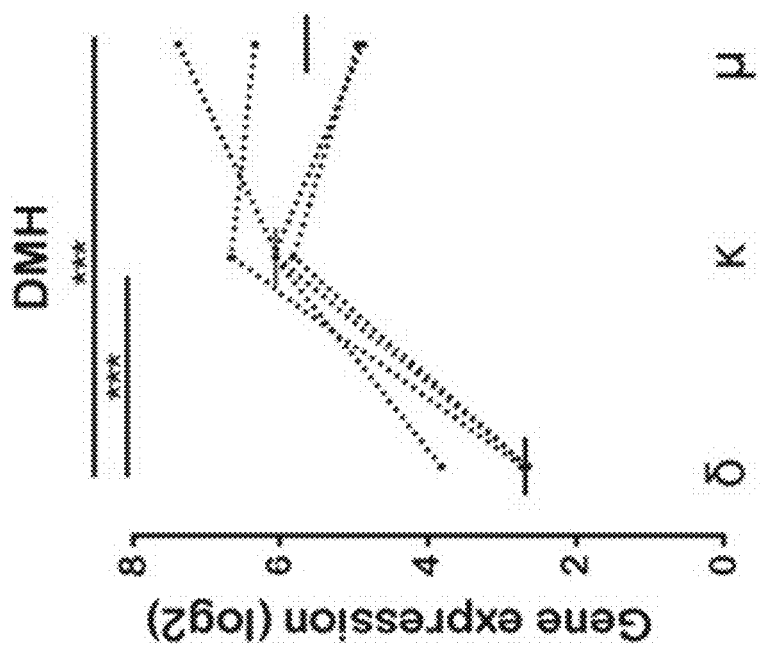
Figure 10G:
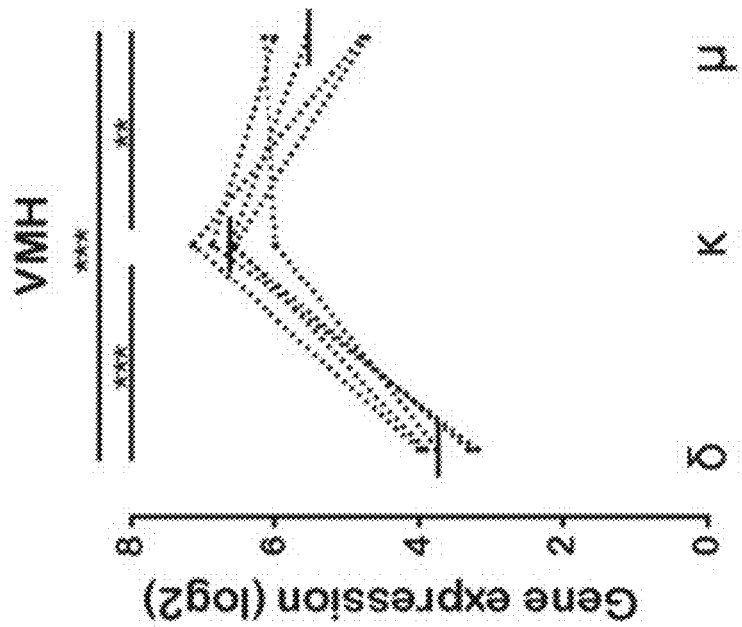
Figure 10H:
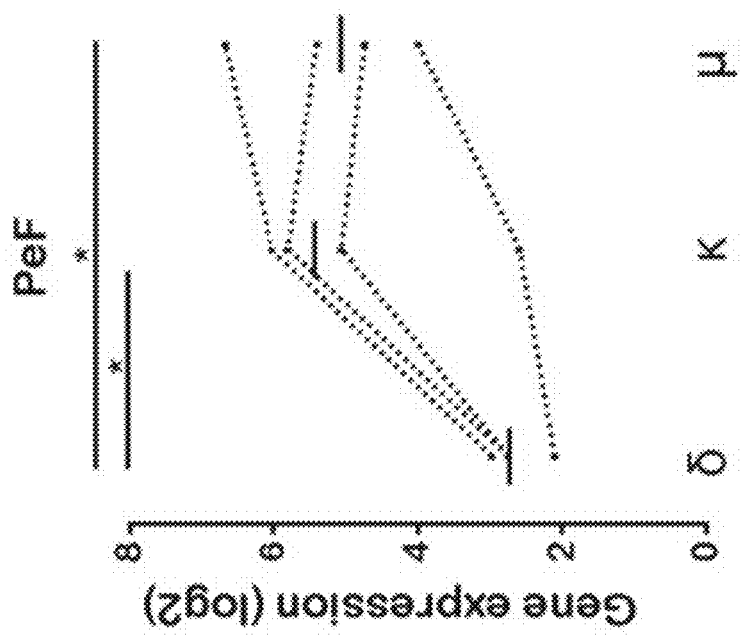
Figure 10K:
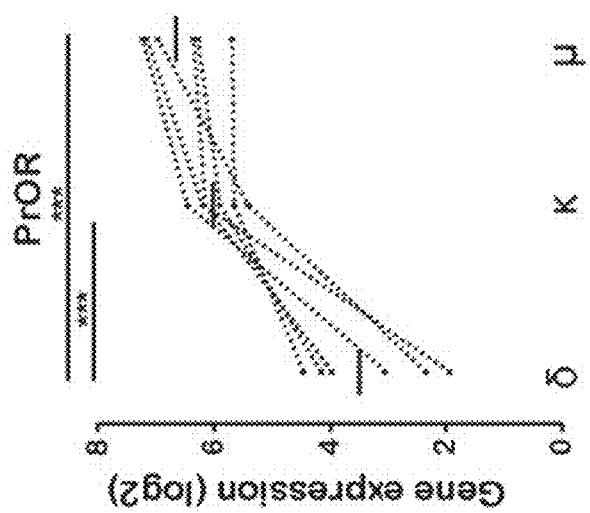
Figure 10J:
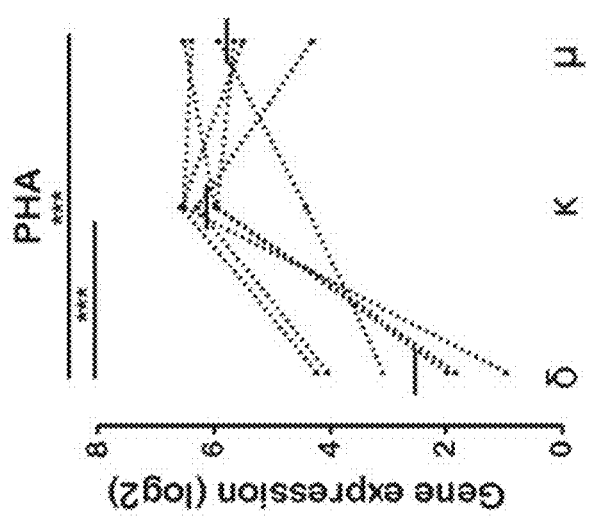
Figure 10I:
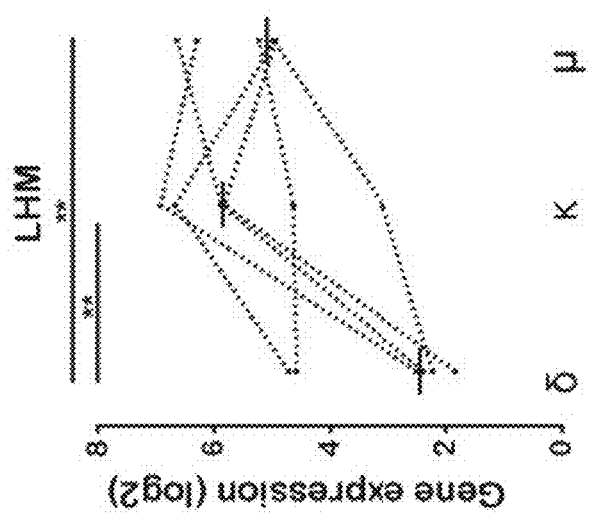
Figure 10L:
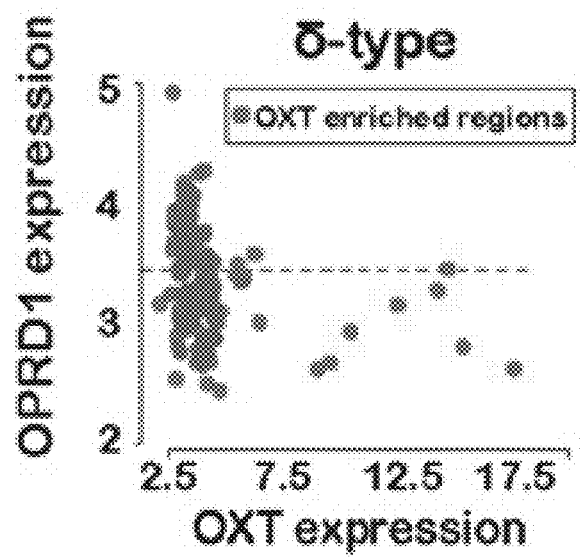
FIGS. 10L-10N are graphs showing that across all 190 regions, μ-opioid and κ-opioid receptors displayed above-average expression within the eight OXT-enriched samples. *P<0.05, P<0.01, *P<0.001.
Figure 10M:
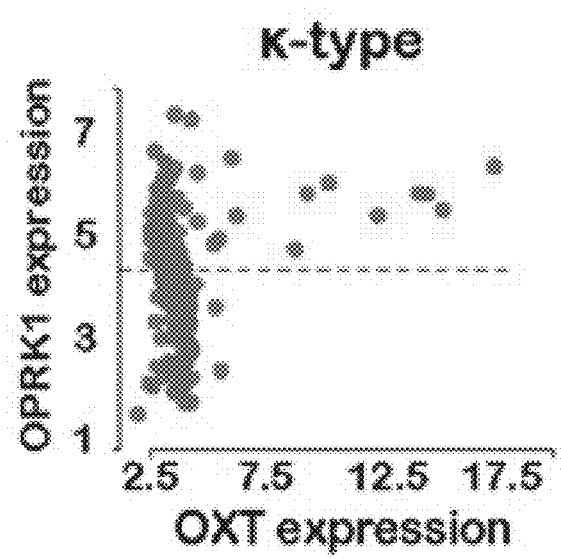
Figure 10N:
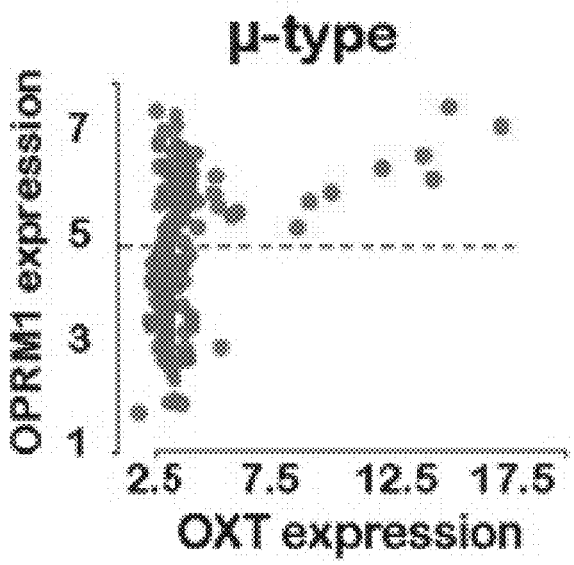
Figure 10O:
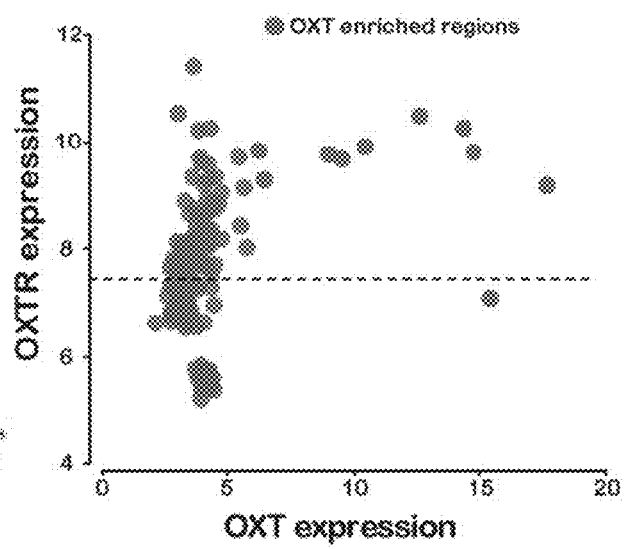

Human Neurogenetics Analysis:

Six postmortem human brains from the Allen Human Brain Atlas were analyzed and downloaded after updated normalization procedures implemented by the Allen Institute in March 2013. For the mRNA dataset, the data can be downloaded directly from the Allen Brain Atlas. Each individual donor's dataset includes normalized microarray expression data. Microarray probes without an Entrez ID were not examined. Probe selection was conducted according to the analysis of Miller, et al., 2014, BMC Genomics 15:154) to analyze probes that most reliably align to RNA-sequencing values, resulting in 20,736 unique gene probes. To prevent biased expression values due to sparse sampling across the six donors, only regions that were sampled in at least four donors were examined. The resulting 190 unique regions and their ontological assignment to each category in FIGS. 10A-10O are documented in Table 1. If more than one sample was present in a given region in a given donor, the microarray expression values were averaged.

To identify regions that most express OXT, microarray data for each of the 190 regions were averaged across subjects. Regions falling 1 SD above the z-transformed mean were identified as "OXT-enriched" (FIGS. 10A-10O). Differences in expression of the μ-opioid (OPRM1), κ-opioid (OPRK1), and σ-opioid (OPRD1) receptor subtypes within each OXT-enriched region were then examined using a within-subject one-way ANOVA (with opioid receptor subtype as a factor) and subsequent multiple comparison tests (false discovery rate Benjamini-Hochberg-corrected). Finally, it was determined whether OPRM1, OPRK1, and OPRD1, as well as OXTR, displayed above-average expression within OXT-enriched regions by plotting their region-wise microarray expression values against the microarray expression values of OXT.

Figure 4B:
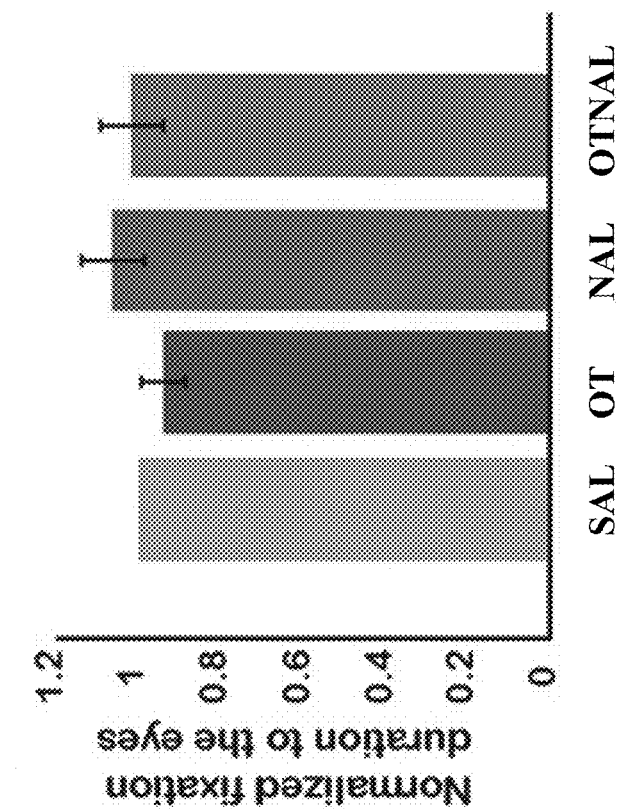
FIGS. 4A-4B are graphs showing drug effects on fixation duration.
Figure 4A:
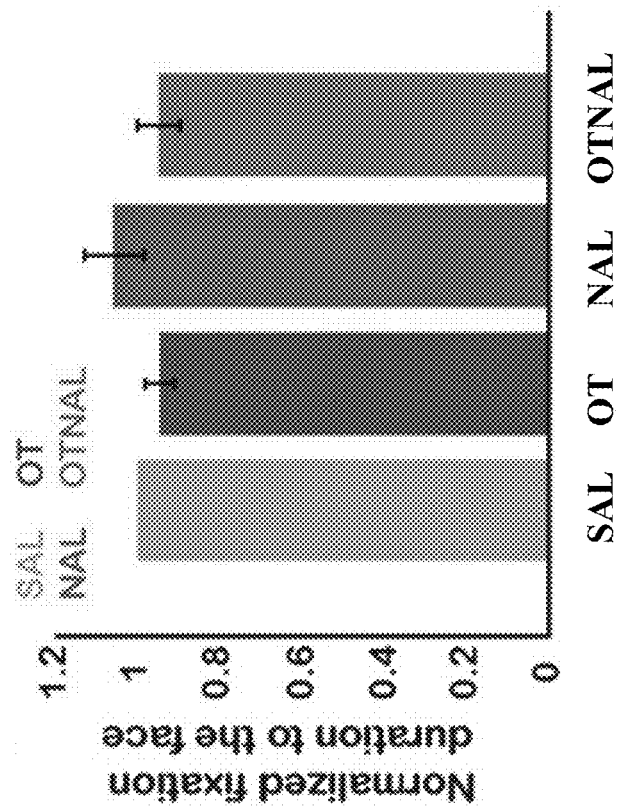
Figure 5A:
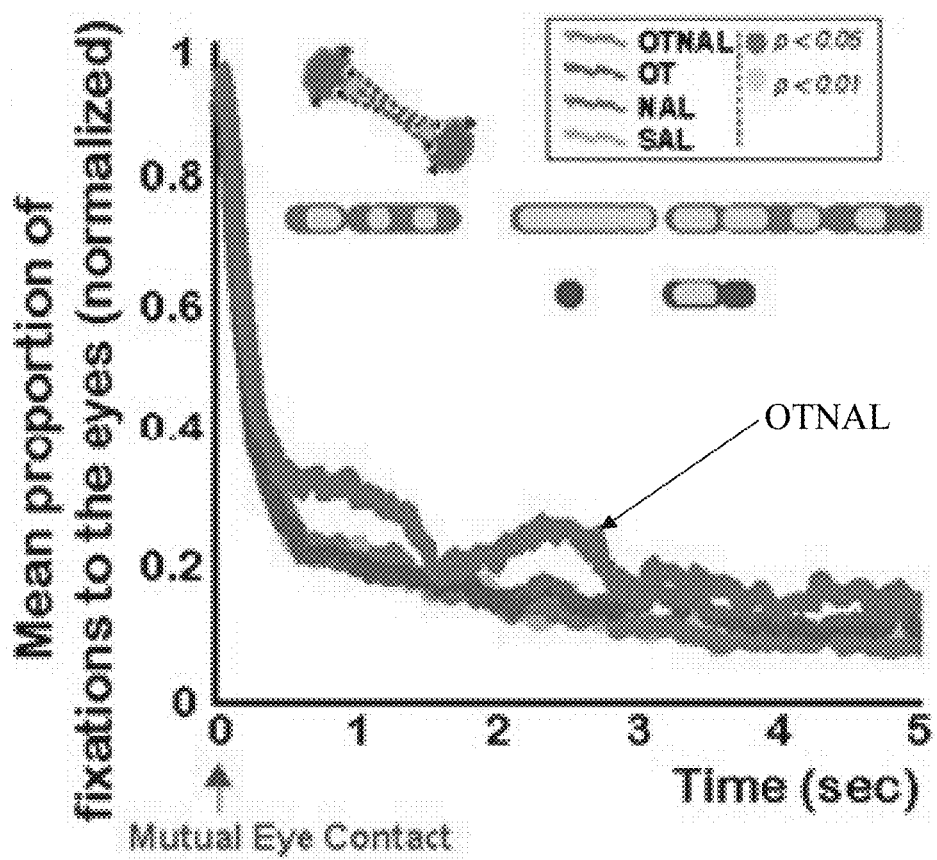
FIGS. 5A-5C are graphs showing supralinear enhancements of dynamic gaze interactions following mutual eye contact by OTNAL.
Figure 5B:
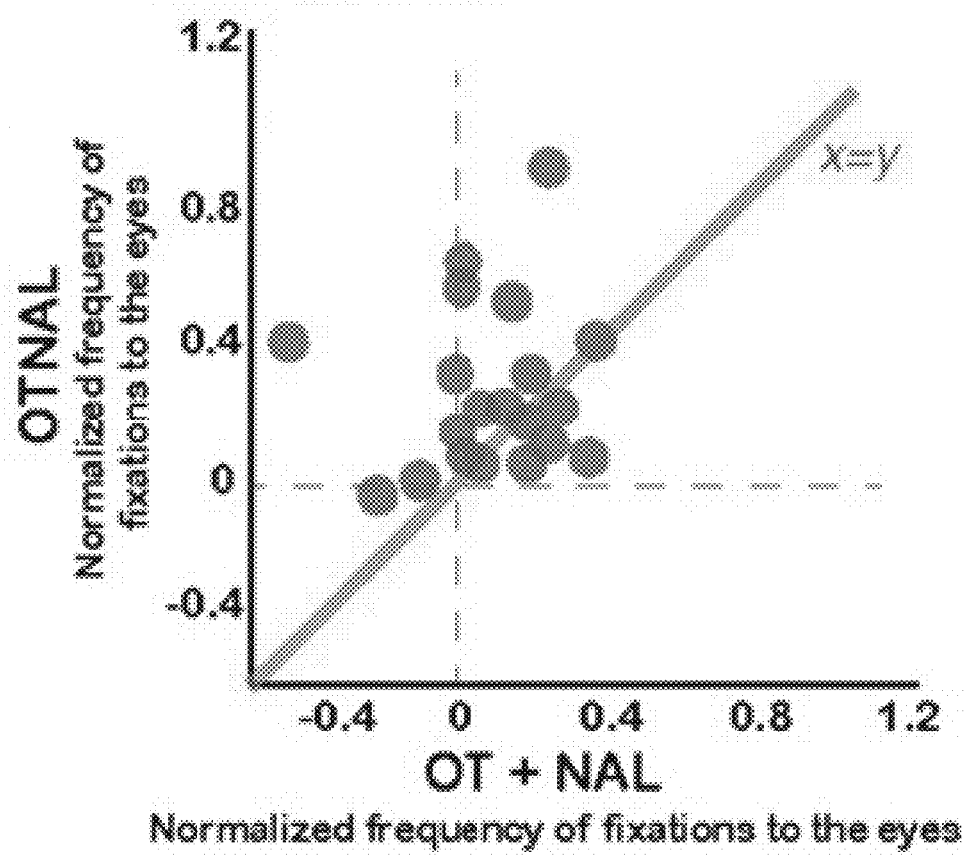
Figure 5C:
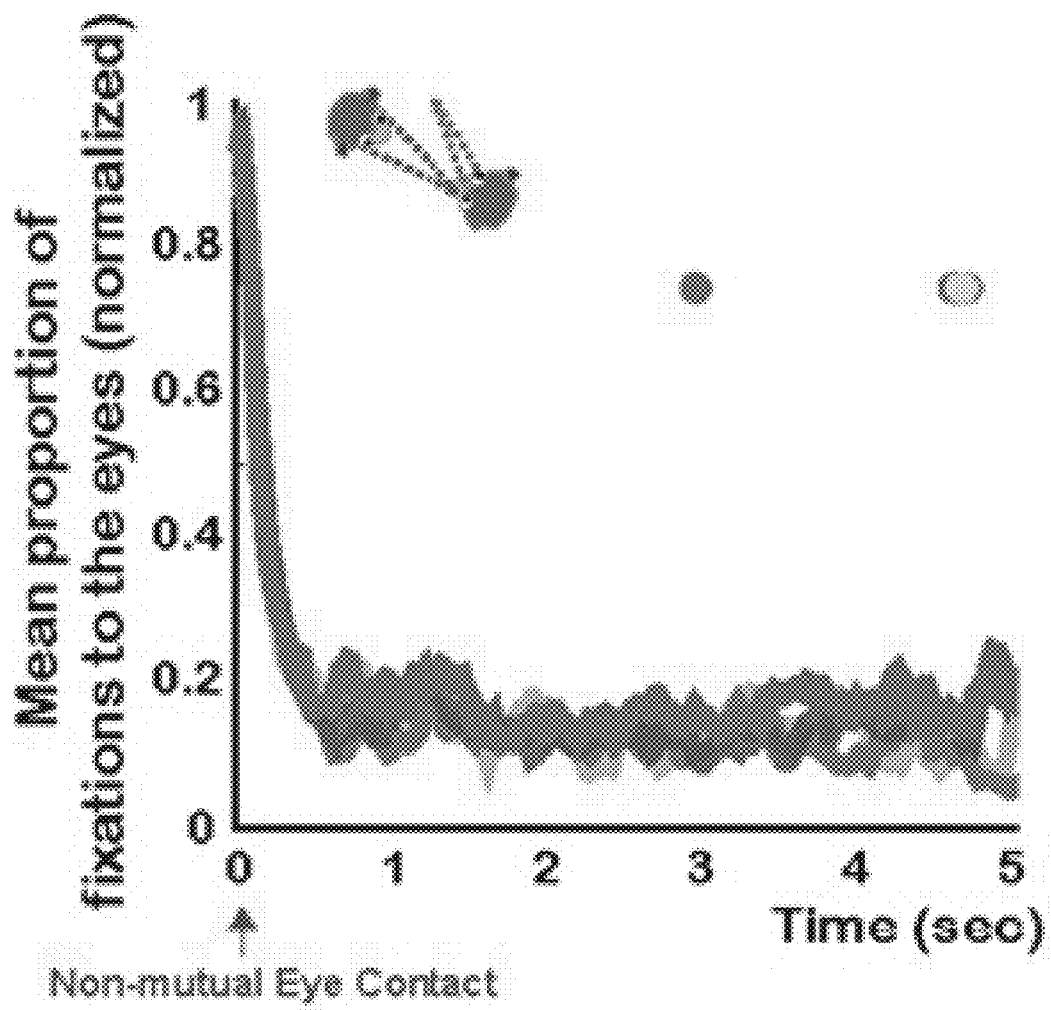

"Structure category" refers to the anatomical ontological category of each tissue sample, which was derived from annotations in the Allen Institute data and is displayed in FIG. 4A. "Structure name" and "Structure acronym" refer to the anatomical name and abbreviation of each tissue sample as it appears in the Allen Institute data.

TABLE 1

| Structure category | Structure name | Acronym |
| --- | --- | --- |
| Frontal lobe | Zona incerta | ZI |
| Frontal lobe | Ventral tegmental area | VTA |
| Frontal lobe | Inferior frontal gyrus, triangular part | trIFG |
| Frontal lobe | Transverse gyri | TG |
| Frontal lobe | Tail of the caudate nucleus | TCd |
| Frontal lobe | Superior temporal gyrus, lateral bank of gyrus | STG-l |
| Frontal lobe | Superior temporal gyrus, inferior bank of gyrus | STG-i |
| Frontal lobe | Superior parietal lobule, superior bank of gyrus | SPL-s |
| Frontal lobe | Superior parietal lobule, inferior bank of gyrus | SPL-i |
| Frontal lobe | Spinal trigeminal nucleus | Sp5 |
| Frontal lobe | Superior occipital gyrus, superior bank of gyrus | SOG-s |
| Frontal lobe | Substantia nigra, pars reticulata | SNR |
| Frontal lobe | Substantia nigra, pars compacta | SNC |
| Frontal lobe | Supramarginal gyrus, superior bank of gyrus | SMG-s |
| Frontal lobe | Supramarginal gyrus, inferior bank of gyrus | SMG-i |
| Frontal lobe | Short insular gyri | SIG |
| Frontal lobe | Superior frontal gyrus, medial bank of gyrus | SFG-m |
| Frontal lobe | Superior frontal gyrus, lateral bank of gyrus | SFG-l |
| Frontal lobe | Subthalamic nucleus | Sb |
| Frontal lobe | Subiculum | S |
| Frontal lobe | Red nucleus | RN |
| Frontal lobe | Raphe nuclei of medulla | RaM |
| Parietal lobe | Reticular nucleus of thalamus | R |
| Parietal lobe | VIIB, paravermis | PV-VIIB |
| Parietal lobe | VI, paravermis | PV-VI |
| Parietal lobe | V, paravermis | PV-V |
| Parietal lobe | IV, paravermis | PV-IV |
| Parietal lobe | Crus II, paravermis | PV-Crus II |

TABLE 1-continued

| Structure category | Structure name | Acronym |
| --- | --- | --- |
| Parietal lobe | Crus I, paravermis | PV-Crus I |
| Parietal lobe | Putamen | Pu |
| Parietal lobe | Preoptic region | PrOR |
| Parietal lobe | Precentral gyrus, superior lateral aspect of gyrus | PrG-sl |
| Parietal lobe | Precentral gyrus, bank of the precentral sulcus | PrG-prc |
| Parietal lobe | Precentral gyrus, inferior lateral aspect of gyrus | PrG-il |
| Temporal lobe | Pontine reticular formation | PRF |
| Temporal lobe | Postcentral gyrus, superior lateral aspect of gyrus | PoG-sl |
| Temporal lobe | Postcentral gyrus, bank of the central sulcus | PoG-cs |
| Temporal lobe | Pontine nuclei | Pn |
| Temporal lobe | Planum polare | PLP |
| Temporal lobe | Parahippocampal gyrus, lateral bank of gyrus | PHG-l |
| Temporal lobe | Parahippocampal gyrus, bank of the cos | PHG-cos |
| Temporal lobe | Posterior hypothalamic area | PHA |
| Temporal lobe | Precuneus, superior lateral bank of gyrus | Pcu-s |
| Temporal lobe | Precuneus, inferior lateral bank of gyrus | Pcu-i |
| Temporal lobe | Paracentral lobule, anterior part, inferior bank of gyrus | PCLa-i |
| Temporal lobe | Occipitotemporal gyrus, superior bank of gyrus | OTG-s |
| Temporal lobe | Occipitotemporal gyrus, inferior bank of gyrus | OTG-i |
| Temporal lobe | Inferior frontal gyrus, orbital part | oriFG |
| Temporal lobe | Middle temporal gyrus, superior bank of gyrus | MTG-s |
| Temporal lobe | Middle temporal gyrus, inferior bank of gyrus | MTP-i |
| Temporal lobe | Medial orbital gyrus | MOrG |
| Occipital lobe | Medial geniculate complex | MG |
| Occipital lobe | Middle frontal gyrus, superior bank of gyrus | MFG-s |
| Occipital lobe | Middle frontal gyrus, inferior bank of gyrus | MFG-i |
| Occipital lobe | Lateral orbital gyrus | LOrG |
| Occipital lobe | Lateral medullary reticular group | LMRt |
| Occipital lobe | Lingual gyrus, striate | LiG-str |
| Occipital lobe | Lingual gyrus, peristriate | LiG-pest |
| Occipital lobe | Long insular gyri | LIG |
| Occipital lobe | Lateral hypothalamic area, mammillary region | LHM |
| Occipital lobe | Dorsal lateral geniculate nucleus | LGd |
| Insula | Lateral nucleus | LA |
| Insula | Inferior temporal gyrus, bank of mts | ITG-mts |
| Cingulate | Inferior temporal gyrus, lateral bank of gyrus | ITG-l |
| Cingulate | Inferior temporal gyrus, bank of the its | ITG-its |
| Cingulate | Inferior olivary complex | IO |
| Cingulate | Rostral group of intralaminar nuclei | ILr |
| Cingulate | Caudal group of intralaminar nuclei | ILc |
| Cingulate | Heschl's gyrus | HG |
| Hippocampus | VIIIA, lateral hemisphere | He-VIIIA |
| Hippocampus | VIIB, lateral hemisphere | He-VIIB |
| Hippocampus | VI, lateral hemisphere | He-VI |
| Hippocampus | Crus II, lateral hemisphere | He-Crus II |
| Hippocampus | Crus I, lateral hemisphere | He-Crus I |
| Hippocampus | Head of the caudate nucleus | HCd |
| Parahippocampus | Gyrus rectus | GRe |
| Parahippocampus | Globus pallidus, internal segment | GPi |
| Amygdala | Gigantocellular group | GiRt |
| Amygdala | Fusiform gyrus, bank of the its | FuG-its |
| Amygdala | Fusiform gyrus, bank of cos | FuG-cos |
| Amygdala | Frontal operculum | fro |
| Amygdala | Posterior group of nuclei | DTP |
| Amygdala | Medial group of nuclei | DTM |
| Basal ganglia | Lateral group of nuclei, ventral division | DTLv |
| Basal ganglia | Lateral group of nuclei, dorsal division | DTLd |
| Basal ganglia | Anterior group of nuclei | DTA |
| Basal ganglia | Dentate nucleus | Dt |

TABLE 1-continued

| Structure category | Structure name | Acronym |
|---|---|---|
| Basal ganglia | Dentate gyrus | DG |
| Basal ganglia | Cuneus, striate | Cun-str |
| Basal ganglia | Cuneus, peristriate | Cun-pest |
| Basal forebrain | Cuneate nucleus | Cu |
| Basal forebrain | Corticomedial group | COMA |
| Basal forebrain | Claustrum | Cl |
| Basal forebrain | Cingulate gyrus, parietal part, superior bank of gyrus | CgGp-s |
| Basal forebrain | Cingulate gyrus, parietal part, inferior bank of gyrus | CgGp-i |
| Basal forebrain | Cingulate gyrus, frontal part, superior bank of gyrus | CgGf-s |
| Mammillary region | Cingulate gyrus, frontal part, inferior bank of gyrus | CgGf-i |
| Mammillary region | Central nucleus | CeA |
| Mammillary region | Corpus callosum | cc |
| Mammillary region | CA4 field | CA4 |
| Mammillary region | CA3 field | CA3 |
| Mammillary region | CA2 field | CA2 |
| Anterior hypothalamic region | CA1 field | CA1 |
| Anterior hypothalamic region | Basomedial nucleus | BMA |
| Anterior hypothalamic region | Basolateral nucleus | BLA |
| Hypothamalus_tuberal | Body of the caudate nucleus | BCd |
| Hypothamalus_tuberal | Amygdalohippocampal transition zone | ATZ |
| Hypothamalus_tuberal | Arcuate nucleus of medulla | Arc |
| Hypothamalus_tuberal | Angular gyrus, superior bank of gyrus | AnG-s |
| Hypothamalus_tuberal | Angular gyrus, inferior bank of gyrus | AnG-i |
| Preoptic region | Nucleus accumbens | Acb |
| Subthalamus | Vestibular nuclei | 8Ve |
| Thalamus | Ventromedial hypothalamic nucleus | VMH |
| Thalamus | Temporal pole, superior aspect | TP-s |
| Thalamus | Temporal pole, medial aspect | TP-m |
| Thalamus | Subcuneiform nucleus | SubCn |
| Thalamus | Nucleus subceruleus | SubC |
| Thalamus | Superior rostral gyrus | SRoG |
| Thalamus | Septal nuclei | SptN |
| Thalamus | Superior occipital gyrus, inferior bank of gyrus | SOG-i |
| Thalamus | Superior olivary complex | SOC |
| Thalamus | Supraoptic nucleus | SO |
| Thalamus | Subcallosal cingulate gyrus | SCG |
| Cerebellum | Pontine rapha nucleus | RPn |
| Cerebellum | Paraventricular nucleus of the hypothalamus | PVH |
| Cerebellum | VIIIB, paravermis | PV-VIIIB |
| Cerebellum | VIIIA, paravermis | PV-VIIIA |
| Cerebellum | IX, paravermis | PV-IX |
| Cerebellum | Precentral gyrus, bank of the central sulcus | PrG-cs |
| Cerebellum | Posterior orbital gyrus | POrG |
| Cerebellum | Postcentral gyrus, bank of the posterior central sulcus | PoG-pcs |
| Cerebellum | Postcentral gyrus, inferior lateral aspect of gyrus | PoG-il |
| Cerebellum | Paracentral lobule, anterior part, superior bank of gyrus | PCLa-s |
| Cerebellum | Parolfactory gyri | PaOG |
| Cerebellum | Medial parabrachial nucleus | MPB |
| Cerebellum | Motor nucleus of trigeminal nerve | Mo5 |
| Cerebellum | Midbrain raphe nuclei | MBRa |
| Cerebellum | Lateral parabrachial nucleus | LPS |
| Cerebellum | Inferior rostral gyrus | IRoG |
| Cerebellum | Inferior occipital gyrus, superior bank of gyrus | IOG-s |
| Cerebellum | Inferior occipital gyrus, inferior bank of gyrus | IOG-i |
| Cerebellum | Globus pallidus, external segment | GPe |
| Cerebellum | Fusiform gyrus, lateral bank of gyrus | FuG-l |
| Cerebellum | Central gray substance of midbrain | CGMB |
| Cerebellum | Cochlear nuclei | 8Co |
| Cerebellum | Facial motor nucleus | 7 |
| Cerebellum | Abducens nucleus | 6 |
| Cerebellum | VIIIB | Ve-VIIIB |
| Cerebellum | VIIIA | Ve-VIIIA |
| Cerebellum | VIIB | Ve-VIIB |
| Cerebellum | VIIAt | Ve-VIIAt |
| Cerebellum | VI | Ve-VI |
| Pons | V | Ve-V |
| Pons | IX | Ve-IX |
| Pons | IV | Ve-IV |
| Pons | III | Ve-III |
| Pons | Temporal pole, inferior aspect | TP-i |
| Pons | Tuberomammillary nucleus | TM |
| Pons | Supramammillary nucleus | SuM |
| Pons | Superior colliculus | SC |
| Pons | III, paravermis | PV-III |
| Pons | Principal sensory nucleus of trigeminal nerve | Pr5 |
| Pons | Planum temporale | PLT |
| Pons | Perifornical nucleus | PeF |
| Midbrain tectum | Inferior frontal gyrus, opercular part | opIFG |
| Midbrain tectum | Olfactory tubercle | OlfT |
| Midbrain tegmentum | Basal nucleus of Meynert | nbM |
| Midbrain tegmentum | Medial mammillary nucleus | MM |
| Midbrain tegmentum | Lateral tuberal nucleus | LTu |
| Midbrain tegmentum | Lateral mammillary nucleus | LM |
| midbrain tegmentum | Lateral hypothalamic area, tuberal region | LHT |
| Midbrain tegmentum | Lateral hypothalamic area, anterior region | LHA |
| Midbrain tegmentum | Locus ceruleus | LC |
| Midbrain tegmentum | Inferior colliculus | IC |
| Midbrain tegmentum | VIIIB, lateral hemisphere | He-VIIIB |
| Claustrum | V, lateral hemisphere | He-V |
| Myelencephalon | IV, lateral hemisphere | He-IV |
| Myelencephalon | Globose nucleus | Glo |
| Myelencephalon | Dorsomedial hypothalamic nucleus | DMH |
| Myelencephalon | Nucleus of the diagonal band, horizontal division | DBv |
| Myelencephalon | Nucleus of the diagonal band, vertical division | DBh |
| Myelencephalon | Cuneiform nucleus | CnF |
| Myelencephalon | Central medullary reticular group | CMRt |
| Myelencephalon | Central glial substance | CGS |
| Myelencephalon | Cingulate gyrus, retrosplenial part, superior bank of gyrus | CgGr-s |
| Myelencephalon | Bed nucleus of stria terminalis | BST |

| Structure category | Structure name | Acronym | HEX |
|---|---|---|---|
| Myelencephalon | Anterior orbital gyrus | AOrG | 9F54A6 |
| Myelencephalon | Oculomotor nuclear complex | 3 | 9F54A6 |
| Myelancephalon | Hypoglossal nucleus | 12 | 9F54A6 |
| White matter | Dorsal motor nucleus of the vagus | 10 | 827E29 |

Example 1: NAL Dose Determination

Figure 2B:
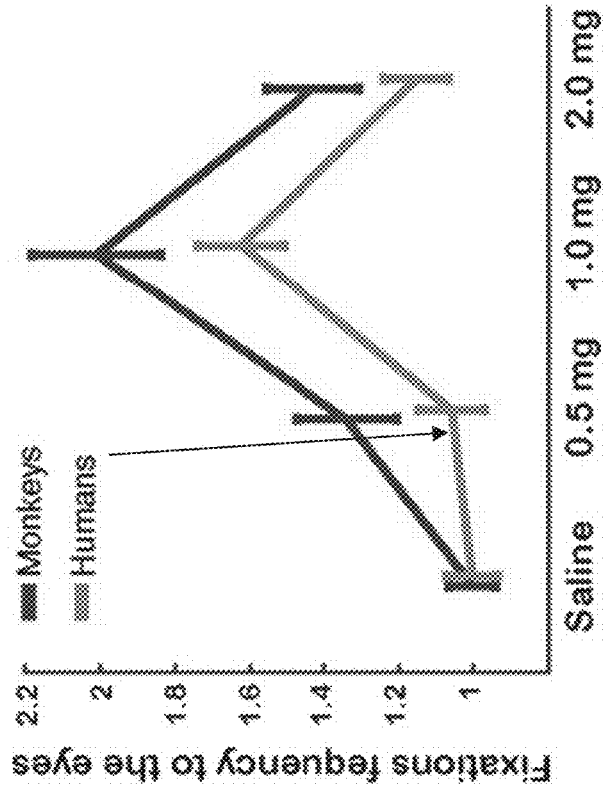
FIGS. 2A-2B are NAL dose-response curves as measured based on fixation frequency.

For testing the behavioral impact of combined delivery of OT and NAL, pairs of monkeys sat directly across from each other while the eye positions from both monkeys were simultaneously and continuously recorded (FIGS. 1A-1B). Using a pediatric nebulizer, one of the animals in a given pair received aerosolized drugs intranasally corresponding to one of the four pharmacology conditions: OT [24 international units (IU)], NAL (1 mg), saline (SAL), or the combination of OT (24 IU) and NAL (1 mg) together (OTNAL) (FIG. 1C and FIGS. 2A-2B).

Figure 2A:
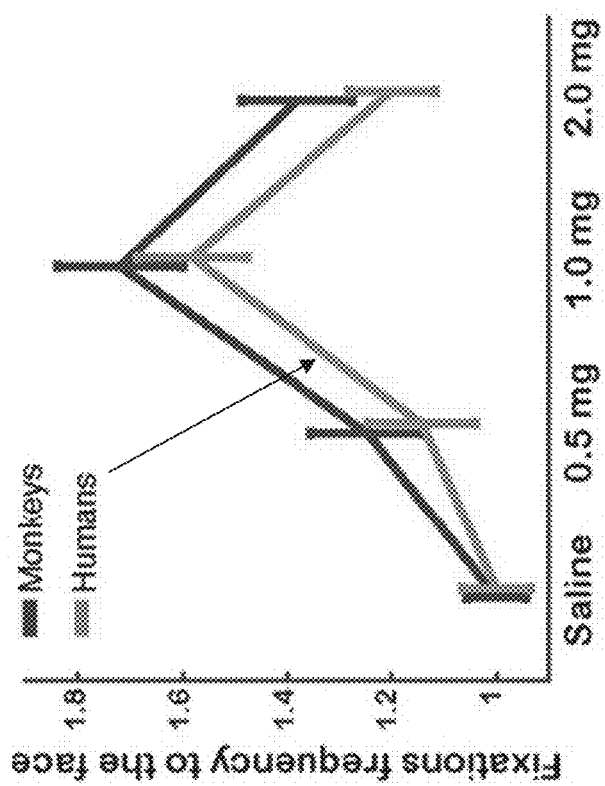

When the three doses of NAL were investigated for fixations to faces, an inverted U-shaped curve was observed, such that maximal effects clearly occurred following the 1-mg dose [FIG. 2A; $F(2,552)=19.2$, $P<0.001$ for main effect of doses, $P<0.001$ for 1 mg over 2 mg, $P<0.001$ for 1 mg over 0.5 mg, $P=0.651$ for 0.5 mg over 2 mg, ANOVA with Tukey-Kramer post hoc tests]. When fixations to the eyes were examined, monkeys overall preferred to look at conspecific eyes compared with human eyes [FIG. 2B; $F(1,546)=8.9$, $P=0.003$ for main effect of images], and the maximal effect again clearly occurred following the 1-mg dose [FIG. 2B; $F(2.546)=13.6$, $P<0.001$ for main effect of doses, $P<0.001$ for 1 mg over 2 mg, $P<0.001$ for 1 mg over 0.5 mg, $P=0.762$ for 0.5 mg over 2 mg, ANOVA with Tukey-Kramer post hoc tests]. NAL administered nasally at the 1-mg dose was used subsequently for the remainder of the study.

Example 2: Fixation Measurements

Figure 3A:
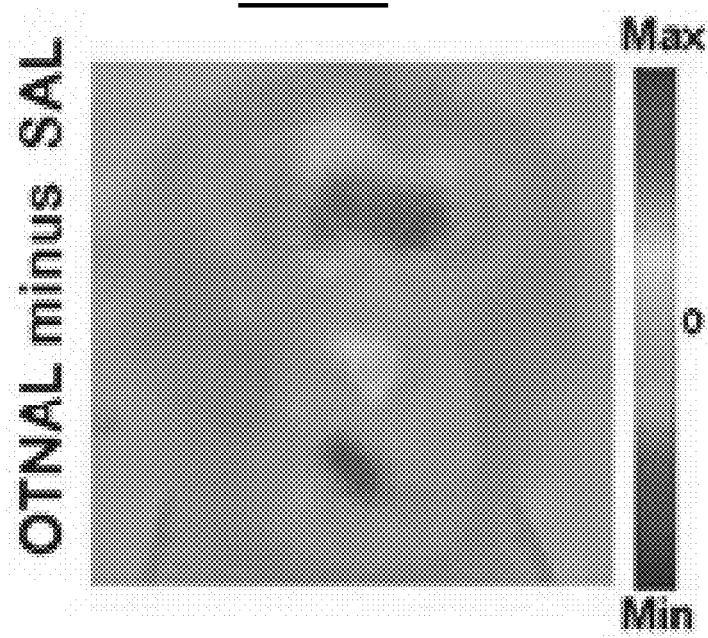
FIGS. 3A-3F are heat-maps and graphs showing the results of combined delivery of OT and NAL. Administration resulted in a supralinear enhancement of overall attention to the face and eyes of a conspecific.
Figure 3B:
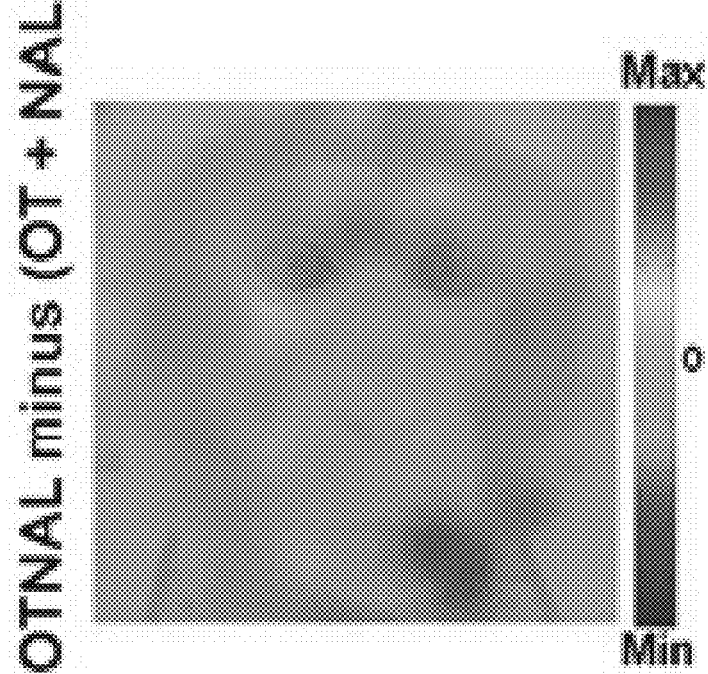
Figure 3C:
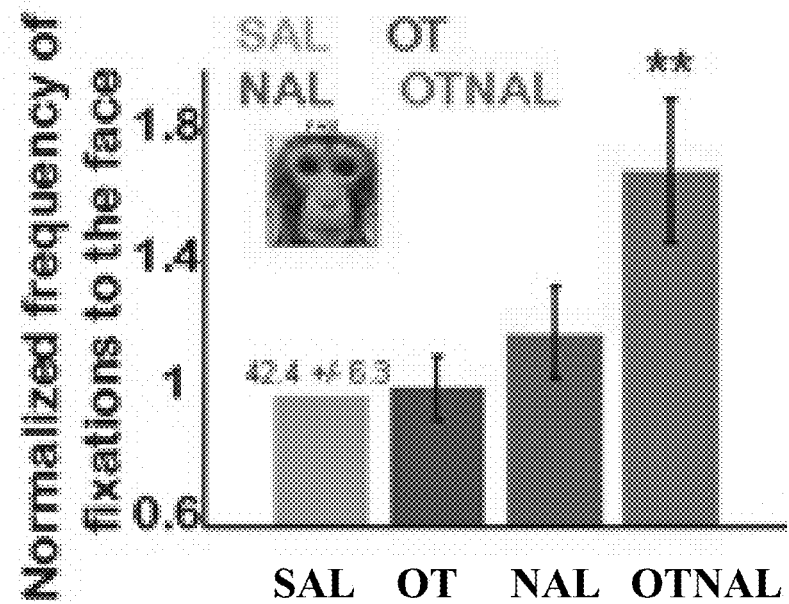
Figure 3D:
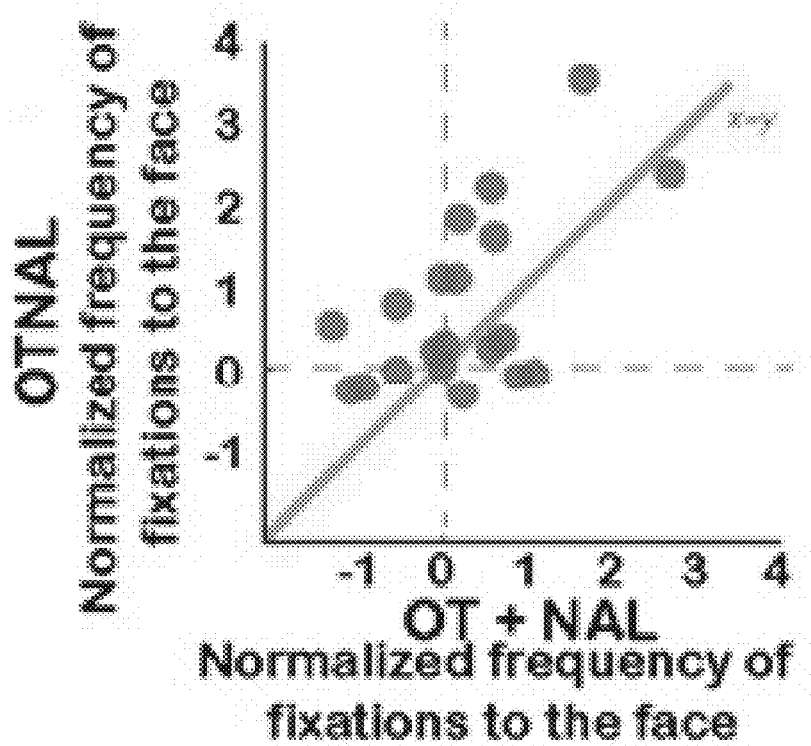
Figure 3E:
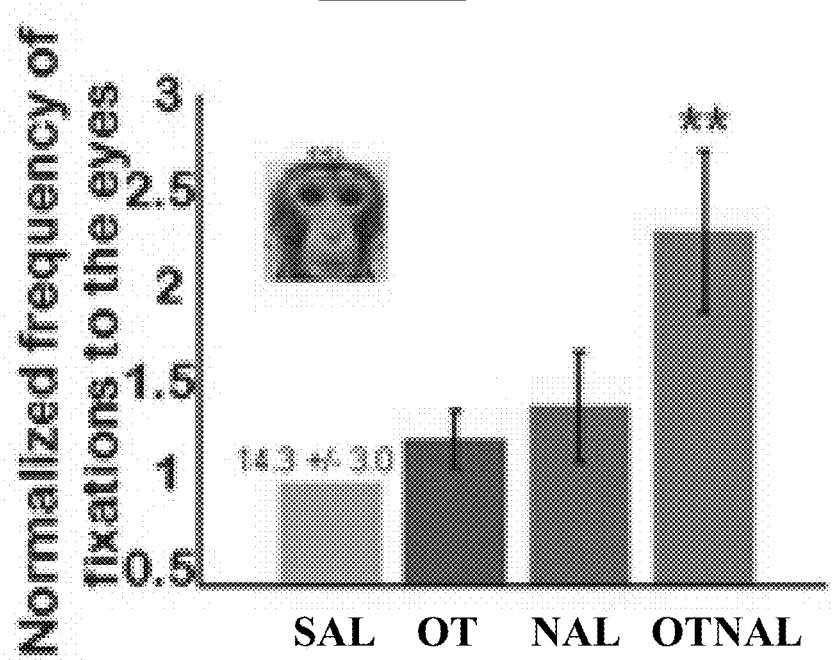
Figure 3F:
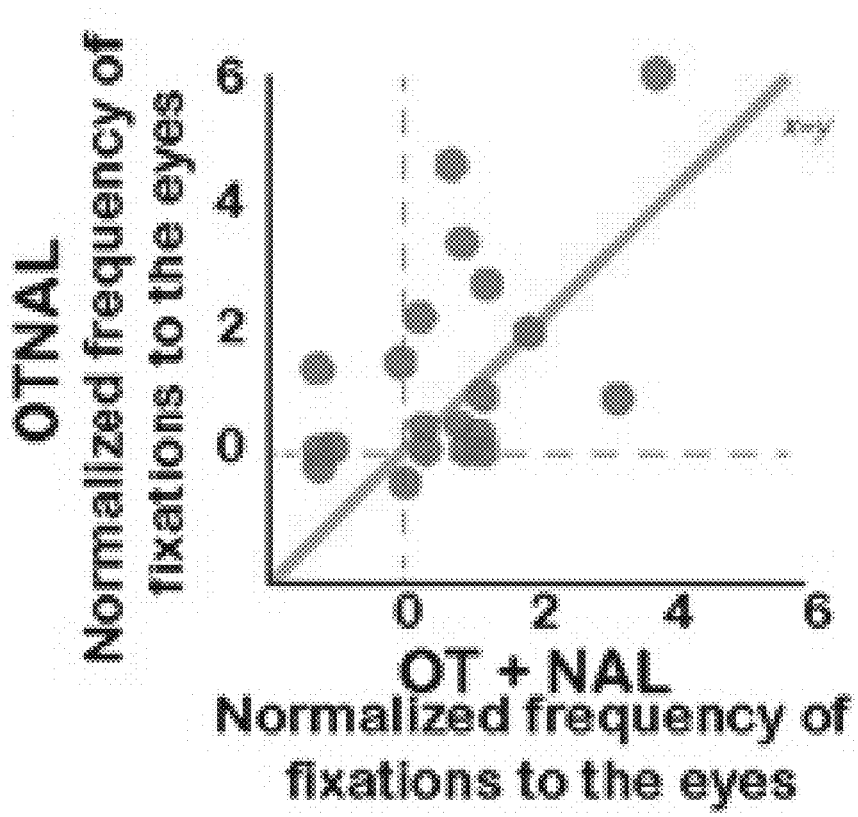

Fixation density maps (FIGS. 3A-3B) showed clear effects of OTNAL that encompass an increase in fixations to the eyes with a relative decrease in fixations to the mouth (FIG. 3A), and those maps suggest a supralinear effect of OTNAL, as shown by an increase in fixations to the eyes after subtracting the effect of OT plus NAL (FIG. 3B). OTNAL was associated with an increased number of fixations to the face of a conspecific compared with the SAL or OT condition [FIG. 3C; $F(3,76)=5.14$, $P=0.003$ for main effect, $P=0.005$ for OTNAL over SAL, $P=0.073$ for OTNAL over NAL, $P=0.007$ for OTNAL over OT, one-way ANOVA with Tukey-Kramer post hoc tests]. To determine whether the effects of OTNAL were supralinear for the conspecific's face, the effects of OTNAL were directly compared with the added effects of OT and NAL alone over SAL control (i.e., a supralinear effect would be indicated by data points reliably falling above the unity line when the OTNAL effects are plotted on the ordinate as a function of the summed effects of OT and NAL on the abscissa). OTNAL had a larger effect for attention to the face than the added effects of OT and NAL alone [FIG. 3D; $t(19)=2.42$, $P=0.026$, paired-sample t test], with the effect size of OTNAL being correlated with the added effect sizes of OT and NAL alone ($r2=0.33$, $P=0.008$; linear regression). Furthermore, the OTNAL condition was associated with increased frequency of fixations to the eyes of a conspecific compared with the SAL or OT condition [FIG. 3E; $F(3,76)=5.87$, $P=0.004$ for main effect, $P=0.004$ for OTNAL over SAL, $P=0.069$ for OTNAL over NAL, $P=0.022$ for OTNAL over OT], again with a supralinear pattern [FIG. 3F; $t(19)=1.94$, $P=0.067$]. This effect size of OTNAL was also correlated with the added effect sizes of OT and NAL alone (for eyes: $r^2=0.29$, $P=0.014$). Critically, both for the face (FIG. 4A) and for the eyes (FIG. 4B), no significant modulation of fixation duration was found for any drug condition relative to SAL, indicating that there was no tradeoff between fixation frequency and fixation duration with respect to the observed effects, and that the effects were specific to increasing fixation frequency across all behavioral sessions to both the face and eyes. Additionally, the supralinear effects of OTNAL could not be explained by a nonspecific increase in arousal, because the total count of fixations in the OTNAL condition was not higher than in the SAL, NAL, or OT conditions (all $P>0.05$, one-way ANOVA with Tukey-Kramer post hoc tests). Finally, in reference to previous literature documenting the effects of OT in social attention, OT overall increased fixations to the eyes compared with SAL in this real-life dyadic setting [FIG. 3E; $t(19)=1.63$, $P=0.059$, paired-sample t test], although the effect was marginal.

A robust increase in the number of fixations to the face and eyes was noted in the OTNAL condition across all of the behavioral sessions. However, it was also important to confirm whether this increase in the number fixations may have been associated with a concurrent decrease in the duration of each individual fixation. To address this concern, the average duration of individual fixations was calculated for each individual pair of monkeys and the effects of drug conditions were compared and normalized to the SAL condition. For both the face and the eyes, no significant modulation of fixation duration was found for any drug condition relative to SAL [FIG. 4A, face: $F(3,76)=1.1$, $P=0.364$ for main effect, all $P>0.410$ for individual comparisons; FIG. 4B, eyes: $F(3,76)=0.84$, $P=0.474$ for main effect, all $P>0.399$ for individual comparisons, one-way ANOVA with Tukey-Kramer post hoc tests]. Thus, the effects of drug condition observed across all of the behavioral sessions appeared to be solely driven by modulations in the number of fixations.

Figure 6A:
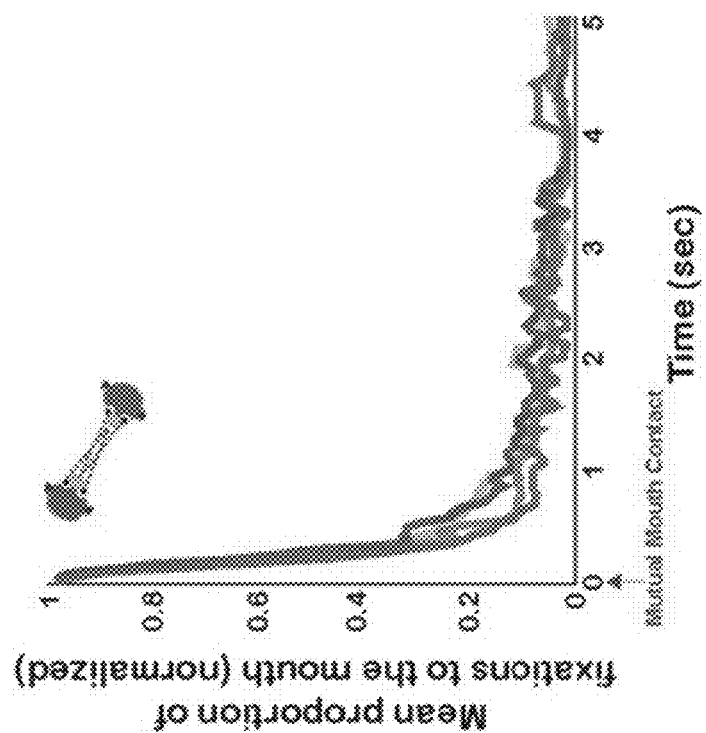
FIGS. 6A-6B are graphs showing attention to the mouth following mutually interactive events in the live gaze interaction task while not modulated by drug condition. Peristimulus time histograms (PSTHs) show the proportions of looking at the mouth following mutual eye contact (FIG. 6A) and looking at the mouth following mutual gaze to the mouth of the conspecific (FIG. 6B) in the SAL (green), OT (blue), NAL (red), and OTNAL (purple) conditions. No 10-ms time bin for any drug condition was significantly higher than for SAL (all P>0.05, paired-sample t tests).
Figure 6B:
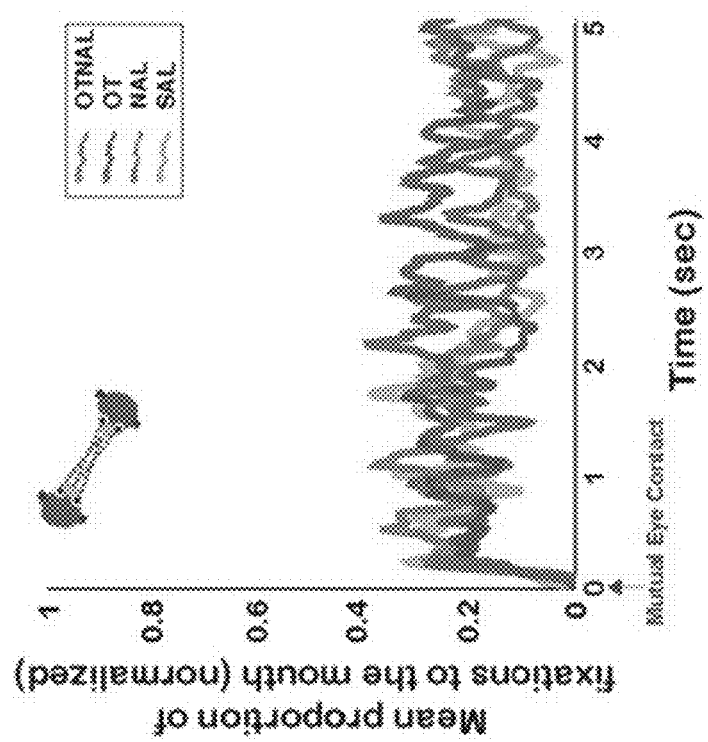
Figure 7A:
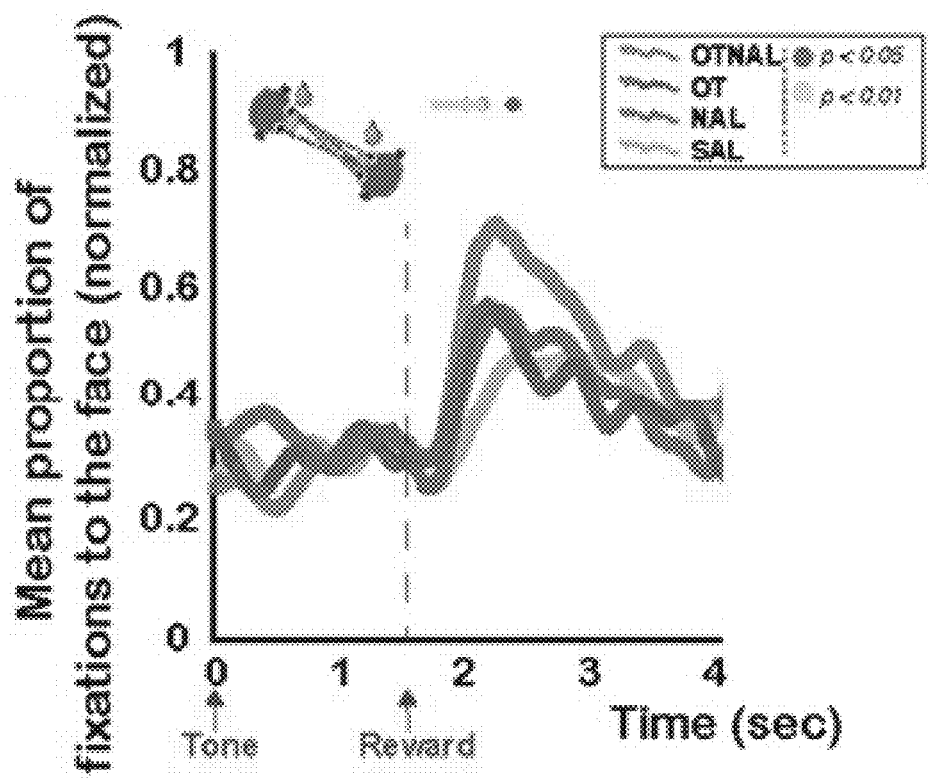
FIGS. 7A-7C are graphs showing supralinear enhancements of dynamic gaze interactions following mutual reward by OTNAL.
Figure 7B:
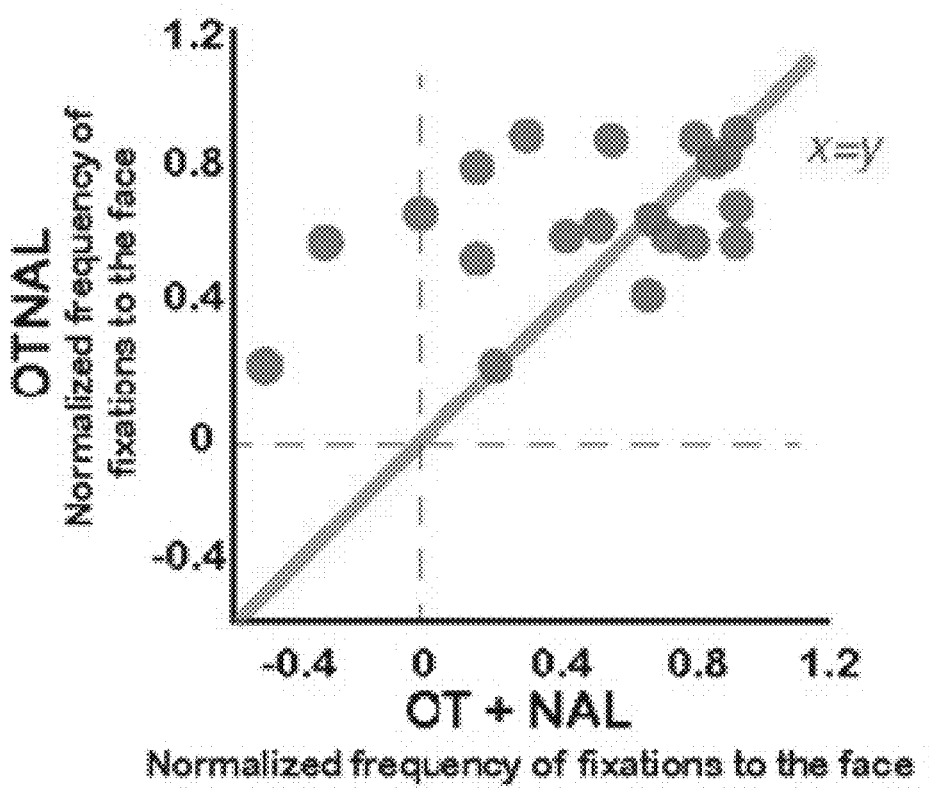
Figure 7C:
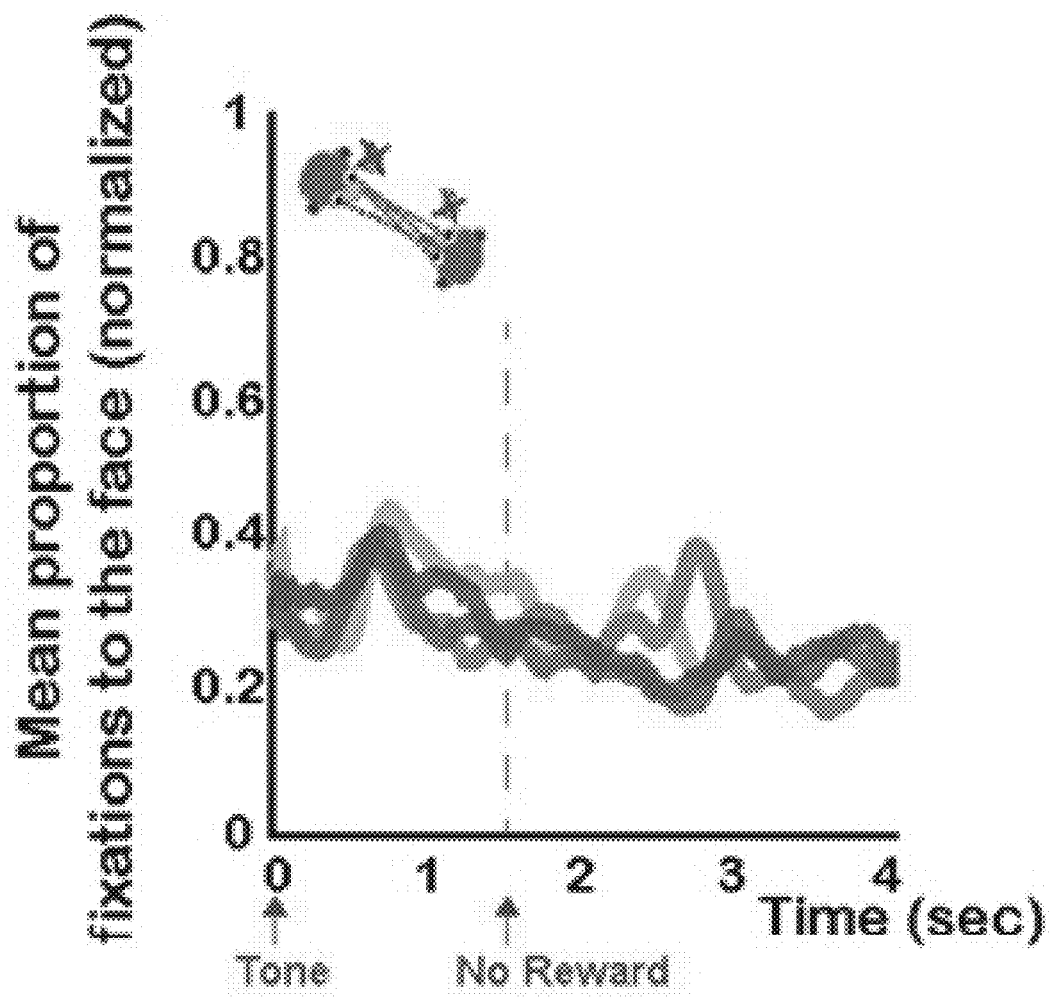
Figures 8A, 8B:
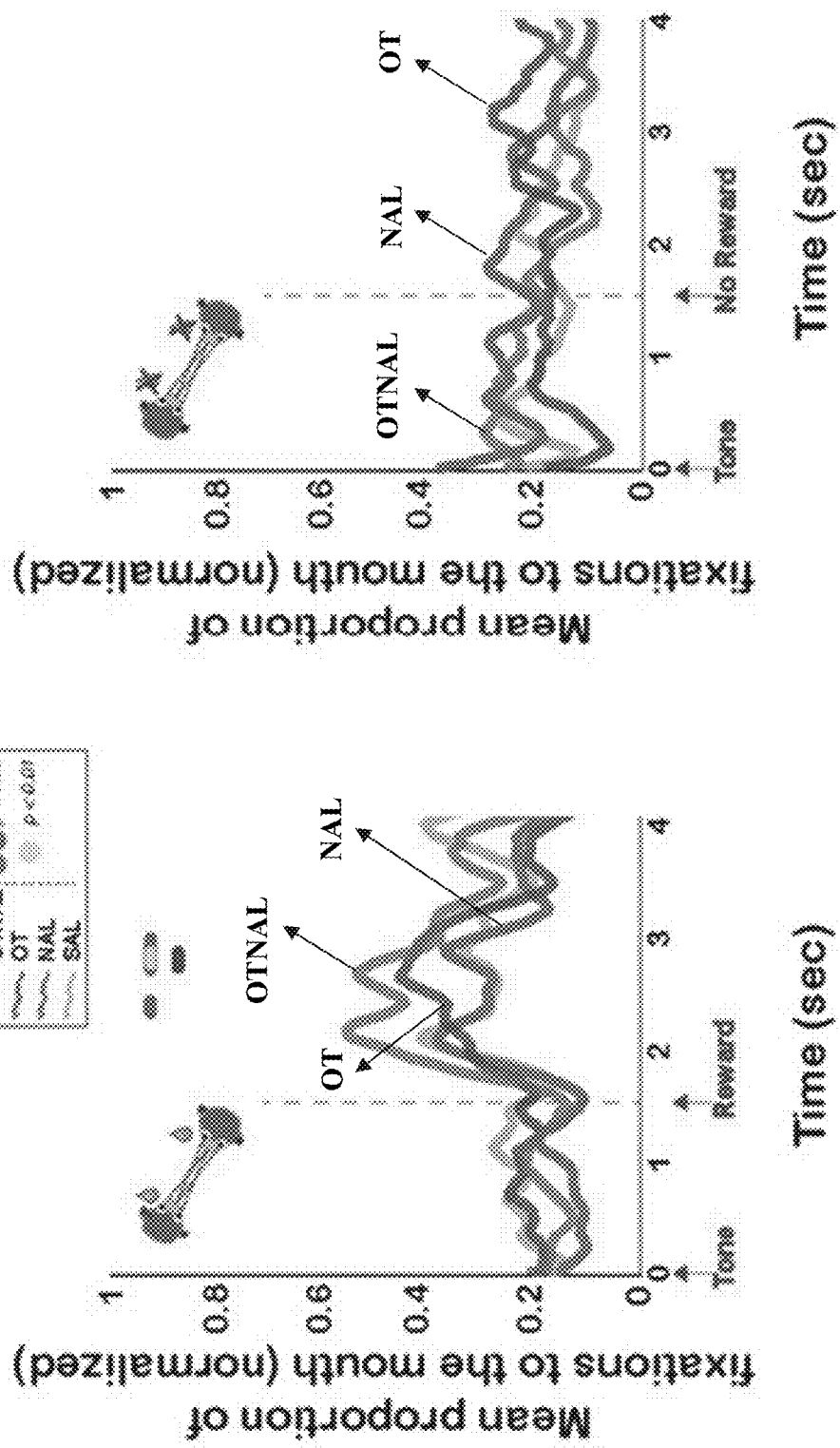
FIGS. 8A-8E are graphs showing that gaze dynamics following mutual reward receipt are driven by the mouth region of the conspecific.
Figure 8C:
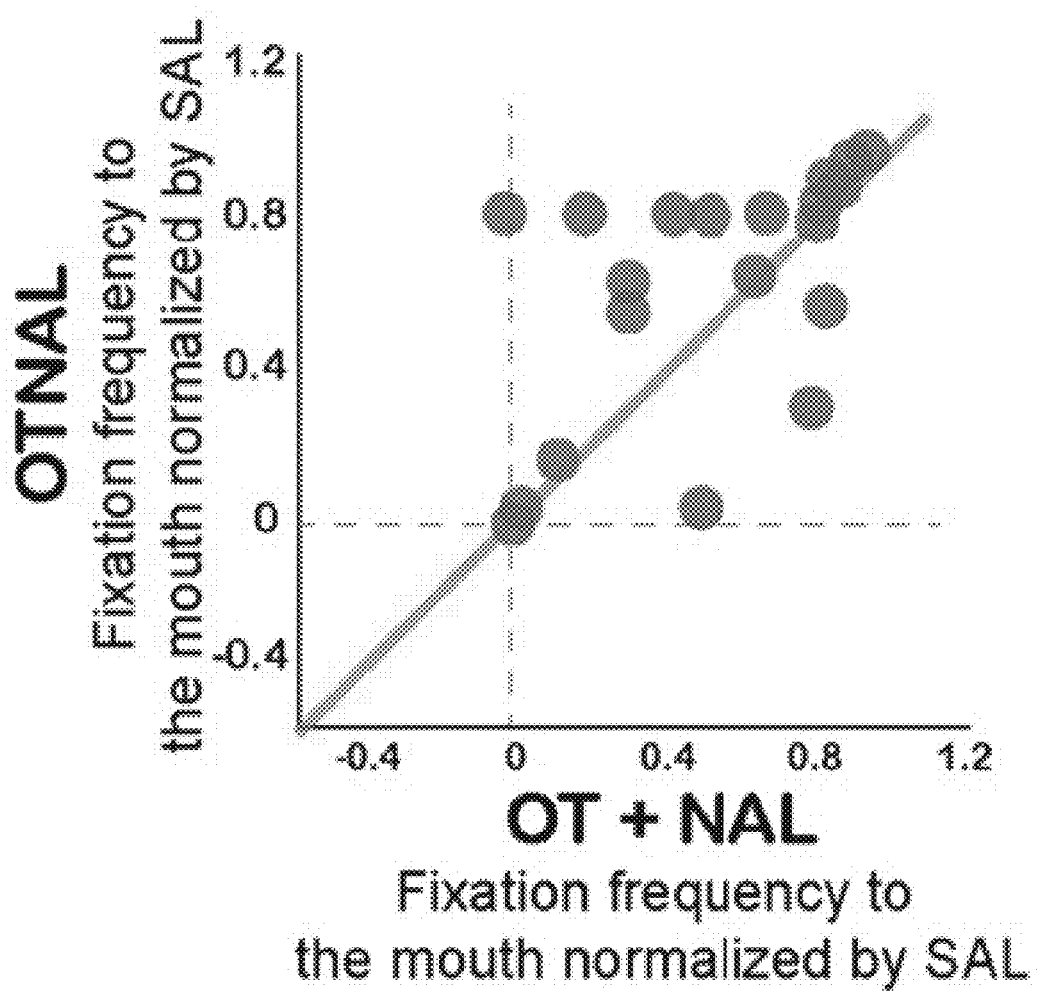
Figure 8D:
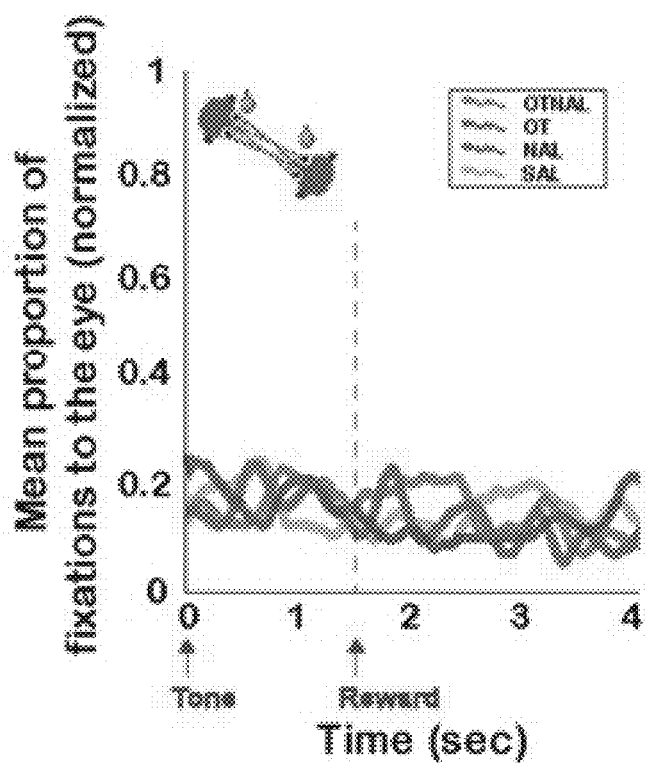
Figure 8E:
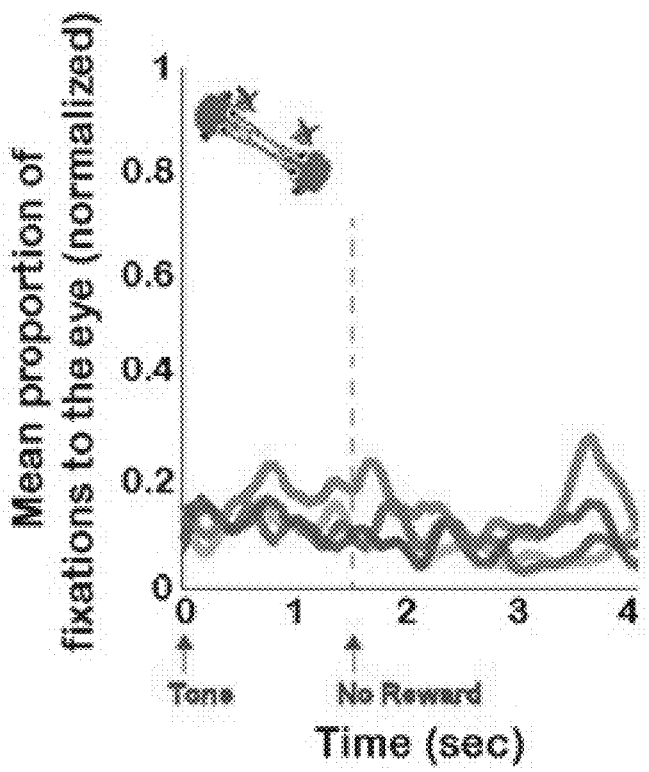

Gaze interactions are by nature dynamic and contingent between interacting agents. Following the pharmacological manipulations, differences in gaze patterns were examined, focusing on time periods following mutual eye contact as instances of particular social importance. Following mutual eye contact, only OTNAL strongly increased attention to the conspecific (FIG. 5A; $P<0.01$, permutation test). In fact, neither OT nor NAL administered alone had a significant effect in increasing attention to the conspecific following mutual eye contact compared with SAL (both $P>0.05$, permutation tests). Notably, when comparing the effects of drugs following mutual eye contact, the resulting gaze patterns were again supralinear [FIG. 5B; $t(19)=2.88$, $P=0.010$, paired-sample t test]. It was then tested whether the effects of OTNAL were specific to the periods following mutual eye contact as opposed to the periods following looking at the conspecific's eyes when the conspecifics were looking elsewhere than the partner's eyes. Following these instances of non-mutual eye contact, no significant results were observed for any pharmacological manipulation using the identical approach (FIG. 5C; all $P>0.05$, permutation tests), indicating that the differences observed in the OTNAL condition selectively occurred during time periods of heightened social relevance. These effects were also observed to be specific to the eye region of interest (ROI), because gaze position returning to the mouth ROI after mutual eye contact, as well as after mutual gaze to the mouth of the conspecific, was not significantly affected by any pharmacological manipulation (FIGS. 6A-6B; all $P>0.05$, permutation tests).

During social interactions, attention can be allocated differentially between interacting individuals depending on the context. For example, a mutually beneficial event is particularly salient to social species living in large groups like macaques and humans, and such a prioritized behavioral relevance may be a foundational component guiding complex social interactions, such as coordinating with one another to obtain mutual benefits. Given the supralinear effects of OTNAL following mutual eye contact, it was hypothesized that similar combinatorial effects of OTNAL following mutual reward receipt by manipulating the receipt of mutual juice rewards during gaze interactions (FIG. 1B). Gaze frequency to the face of the conspecific was only significant in the OTNAL condition (FIG. 7A; $P<0.001$, permutation test). Notably, these effects were again supralinear following mutual reward for OTNAL compared with the summed effects of OT and NAL, with a positive correlation between them [FIG. 7B; $t(19)=2.14$, $P=0.046$, paired-sample t test; $r^2=0.25$, $P=0.023$, linear regression]. By contrast, when no reward was delivered to either animal, no modulations in gaze behaviors were found across all conditions (FIG. 7C; all $P>0.05$, permutation tests), indicating that OTNAL also supralinearly influenced social gaze dynamics following mutually beneficial events.

Across mutual eye contact (FIGS. 5A-5C) and mutual reward receipt (FIGS. 7A-7C), the supralinear effects of OTNAL were driven by the most socially relevant features within the face of the conspecific, depending on the context of a given interactive event. Although the differences in gaze patterns following mutual eye contact in the OTNAL condition were specifically driven by returning gaze to the eye ROI (FIG. 5A and FIGS. 6A-6B), the differences following mutual reward were specifically driven by attention to the mouth ROI (FIGS. 8A-8E). Therefore, the supralinear effects of OTNAL are selective in that they were exerted by the most relevant features within the face of the conspecific depending on the interactive context.

Example 3: Sex Differences

Figure 9A:
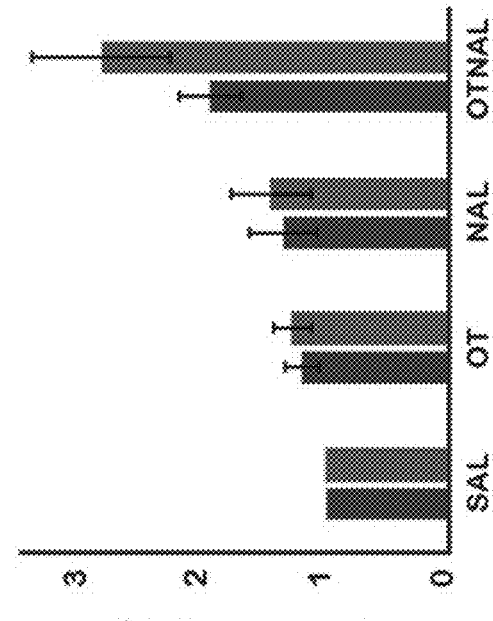
FIG. 9A-9D are graphs showing sex differences in the gaze studies.

Although the number of males and females tested in the study was underpowered for fully exploring potential sex difference, when fixation frequency to the face (FIG. 9A) and eyes (FIG. 9B) was analyzed over entire behavioral sessions, as well as gaze dynamics to the conspecific following mutual eye contact (FIG. 9C) and mutual reward (FIG. 9D), no significant effect of sex was found. Together, these results show that, within our limited sample size, drug effects are observed indistinguishably across both sexes.

The monkeys were separated based on sex, and the data was reanalyzed with both drug effect and the sex of the subject included as factors of interest for all of positive results, including the increase in gaze to the face and eyes across all of the behavioral sessions, as well as increased attention to the conspecific following mutual eye contact and mutual reward. When analyzing the number of fixations to the face and eyes of a conspecific across all of the behavioral sessions, no significant effect of sex was found between animals within the SAL condition [face: 46.4±8.1 fixations for males, 36.4±10.1 fixations for females, $t(18)=0.78$, $P=0.447$; eyes: 17.4±4.3 fixations for males, 9.5±3.2 fixations for females, $t(18)=1.35$, $P=0.193$, two-sample t test]. A significant main effect of drug condition was noted, but no significant main effect of sex or an interaction between these two factors was observed [FIGS. 9A-9B; face: main effect of drug $F(3,72)=5.6$, $P=0.002$; main effect of sex $F(1,72)=0.17$, $P=0.679$; interaction between drug and sex $F(3,72)=0.91$, $P=0.442$; eyes: main effect of drug $F(3,72)=5.3$, $P=0.002$; main effect of sex $F(1,72)=1.03$, $P=0.314$; interaction between drug and sex $F(3,72)=0.62$, $P=0.603$, two-way ANOVA with drug condition and sex as factors].

Figure 9C:
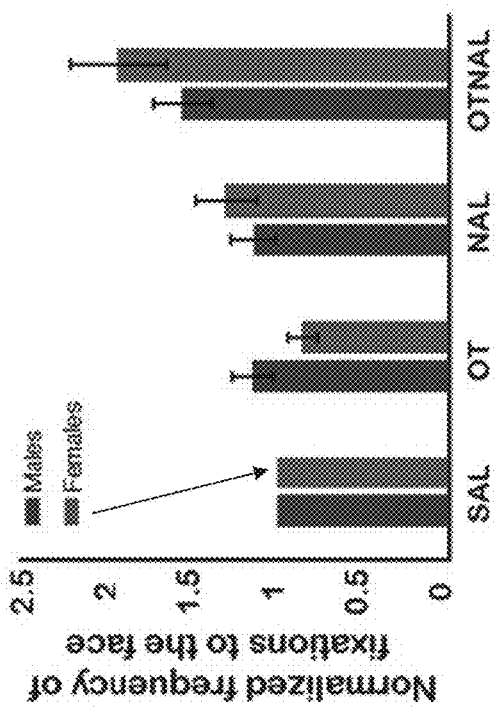
Figure 9B:
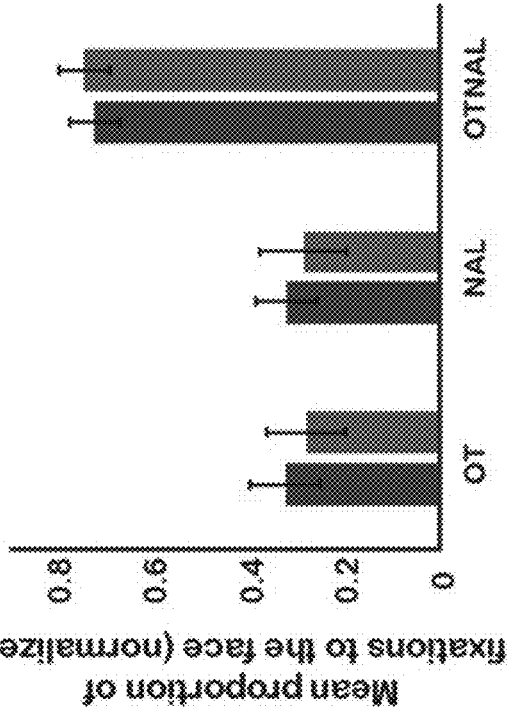
Figure 9D:
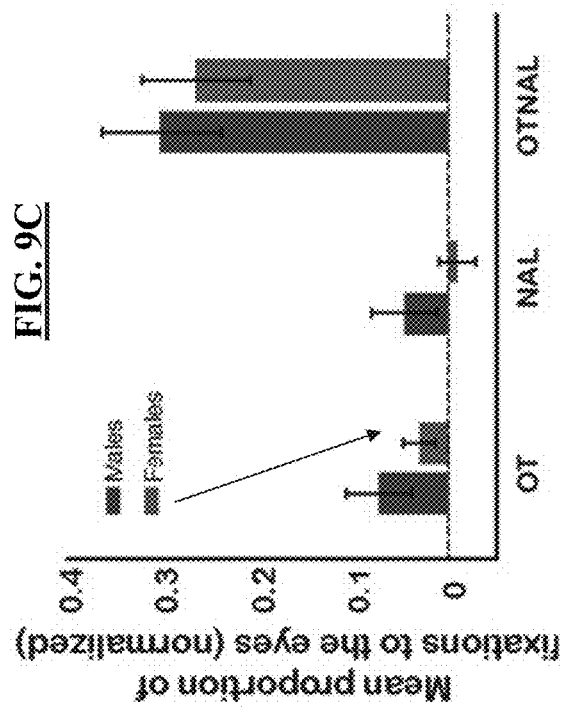

When analyzing gaze to the conspecific following mutual eye contact and mutual reward, again, no significant effect of sex was found between animals within the SAL condition [mutual eye contact: 0.097±0.030 proportion of looking for males, 0.036±0.015 proportion of looking for females, $t(18)=1.19$, $P=0.249$; mutual reward: 0.445±0.081 proportion of looking for males, 0.506±0.056 proportion of looking for females, $t(18)=0.41$, $P=0.686$, two-sample t test][FIGS. 9C-9D; mutual eye contact: main effect of drug $F(2,54)=11.2$, $P<0.0001$; main effect of sex $F(1,54)=0.82$, $P=0.368$; interaction between drug and sex $F(2,54)=0.0004$, $P=0.989$; mutual reward: main effect of drug $F(2,54)=11.9$, $P<0.0001$; main effect of sex $F(1,54)=0.005$, $P=0.816$; interaction between drug and sex $F(2,54)=0.006$, $P=0.942$, two-way ANOVA with drug condition and sex as factors]. Together, these results showed that within the limited sample size, drug effects are observed indistinguishably across both sexes.

Example 4: Human Neurogenetics Analysis

Potential brain regions underlying the facilitatory effects of opioid antagonism on OT in the human brain were examined. Colocalization of gene expression patterns for the OT gene (OXT); OT receptor gene (OXTR); and μ-opioid (OPRM1), κ-opioid (OPRK1), and δ-opioid (OPRD1) receptor subtypes, were examined using averaged microarray expression data of six postmortem donors from the Allen Human Brain Atlas. Available data included 190 regions containing samples from at least four donors. Transcription of the OXT was most pronounced in 10 regions displaying expression ≥1 SD above the region-wise mean [FIG. 10A; lateral hypothalamic area, tuberal region (LHT); paraventricular nucleus of the hypothalamus (PVH); supraoptic nucleus (SO); dorsomedial hypothalamic nucleus; lateral hypothalamic area, anterior region; lateral hypothalamic area, medial region; ventral hypothalamic area, medial region; perifornical nucleus; posterior hypothalamic area; and preoptic region].

Comparing the relative expression of OPRM1, OPRK1, and OPRD1 among the 10 highest OXT-enriched regions responsible for endogenous OT release, significant main effects of opioid receptor subtype in each region were found (FIGS. 10B-10K). In all of these OXT-enriched regions, OPRM1 and OPRK1 displayed significantly greater expression than OPRD1 (FIGS. 10B-10K). The effects of opioid receptor subtype were particularly pronounced in the three regions with greatest OXT expression: LHT [$F(1,3)=54.64$, $P=0.005$ for main effect, $P=0.002$ for μ over δ, $P=0.002$ for κ over δ, $P=0.691$ for μ over κ, one-way within subjects ANOVA with Benjamini-Hochberg corrected post hoc tests)], PVH [$F(1,4)=39.05$, $P=0.003$ for main effect, $P<0.001$ for μ over δ, $P<0.001$ for κ over δ, $P=0.201$ for μ over κ], and SO [$F(1,4)=97.15$, $P<0.001$ for main effect, $P<0.001$ for μ over δ, $P<0.001$ for κ over δ, $P=0.005$ for μ over κ]. Robust above-average expression of OPRM1 and OPRK1 genes, but not OPRD1, was observed in all 10 OXT-enriched regions (FIGS. 10L-10N). Notably, the expression levels for OPRM1 and OXT in the 10 OXT-enriched regions were correlated [$r(8)=0.88$, $P<0.001$, Pearson's correlation; FIGS. 10L-10N], whereas there were no such correlations for OPRK1 [$r(8)=0.15$, $P=0.673$] and OPRD1 [$r(8)=-0.17$, $P=0.632$], insinuating a tighter coupling between OXT and OPRM1. Moreover, above-average expression of OXTR in the OXT-enriched regions was also reliably observed (FIG. 10A and FIG. 10O), suggesting a regional co-localization of OXT, OXTR, OPMR1, and OPRK1. Taken together, these results indicate the preferential role of μ-opioid and κ-opioid receptor subtypes in OT-secreting brain regions.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of increasing or delaying decrease of social cognition in a subject,
the method comprising administering to the subject
a therapeutically effective amount of oxytocin and
a therapeutically effective amount of at least one opioid antagonist selected from naloxone (NAL), nalmefene, diprenorphine, nalorphine, nalorphine dinicotinate, levallorphan, samidorphan, nalodiene, buprenorphine, dezocine, eptazocine, butorphanol, levorphanol, nalbuphine, pentazocine, phenazocine, cyprodime, naltrindole, norbinaltorphimine, and prodrugs, salts, and solvates thereof.

2. The method of claim 1, wherein the method treats at least one social function disorder in the subject.

3. The method of claim 2, wherein the at least one social function disorder is selected from autism, autism spectrum disorders (ASD), Asperger's syndrome, pervasive developmental disorder not otherwise specified (PDD-NOS), Rett's disorder, childhood disintegrative disorder (CDD), semantic communication disorder, non-verbal learning disabilities, hyperlexia, schizophrenia, addiction, attention deficit disorder (ADD), depression, bi-polar depression, anxiety disorders, psychopathy, and post-traumatic stress disorder (PTSD).

4. The method of claim 1, wherein the subject is administered about 0.4 µg/kg to about 0.8 µg/kg (oxytocin/subject weight).

5. The method of claim 1, wherein the subject is administered about 0.1 µg/kg to about 10 µg/kg (oxytocin/subject weight).

6. The method of claim 1, wherein the subject is administered about 24 µg to about 96 µg oxytocin.

7. The method of claim 1, wherein the subject is administered about 48 µg oxytocin.

8. The method of claim 1, wherein the subject is administered about 0.001 mg/kg to about 1 mg/kg of the at least one opioid antagonist.

9. The method of claim 1, wherein the subject is administered about 0.01 mg/kg to about 0.1 mg/kg of the at least one opioid antagonist.

10. The method of claim 1, wherein the subject is administered about 0.25 mg to about 4 mg of the at least one opioid antagonist.

11. The method of claim 1, wherein the subject is administered about 1 mg of the at least one opioid antagonist.

12. The method of claim 1, wherein the oxytocin and the at least one opioid antagonist are independently administered to the subject through a route selected from inhalational, oral, nasal, rectal, parenteral, sublingual, transdermal, transmucosal intravesical, intrapulmonary, intraduodenal, intragastrical, intrathecal, epidural, intrapleural, intraperitoneal, subcutaneous, intramuscular, intradermal, intra-arterial, intravenous, intrabronchial, inhalation, and topical administration.

13. The method of claim 1, wherein the administration of the oxytocin and the at least one opioid antagonist is intranasal.

14. The method of claim 1, wherein the oxytocin and the at least one opioid antagonist are co-formulated as part of a pharmaceutical composition further comprising at least one pharmaceutical carrier.

15. The method of claim 14, wherein the pharmaceutical composition is administered intranasally to the subject using an apparatus or device capable of aerosolizing the pharmaceutical composition.

16. The method of claim 15, wherein the apparatus or device is at least one selected from a nebulizer, an inhalator, a humidifier, an inhaler, a nasal sprayer, a mister, and an atomizer.

17. The method of claim 1, wherein the subject is a mammal.

18. The method of claim 17, wherein the subject is a human.

* * * * *

UNITED STATES PATENT AND TRADEMARK OFFICE
CERTIFICATE OF CORRECTION

PATENT NO. : 11,160,843 B2
APPLICATION NO. : 16/398744
DATED : November 2, 2021
INVENTOR(S) : Wohn Chul Chang, Olga Dal Monte and Matthew Piva It is certified that error appears in the above-identified patent and that said Letters Patent is hereby corrected as shown below:

On the Title Page

The first named inventor is listed as: Wohn Chui Chang
The correct spelling of the inventor is: Wohn Chul Chang Signed and Sealed this
First Day of August, 2023

Katherine Kelly Vidal
*Director of the United States Patent and Trademark Office*

SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence

```
<220> FEATURE:
<223> OTHER INFORMATION: Chemically synthesized
<220> FEATURE:
<221> NAME/KEY: DISULFID
<222> LOCATION: (1)..(1)
<223> OTHER INFORMATION: Cys1 forms a disulfide bond with Cys6
<220> FEATURE:
<221> NAME/KEY: MOD_RES
<222> LOCATION: (9)..(9)
<223> OTHER INFORMATION: AMIDATION

<400> SEQUENCE: 1

Cys Tyr Ile Gln Asn Cys Pro Leu Gly
1               5
```